US011264590B2

(12) United States Patent
Gao et al.

(10) Patent No.: US 11,264,590 B2
(45) Date of Patent: Mar. 1, 2022

(54) BENZO DIHETEROCYCLIC COMPOUND, DISPLAY PANEL, AND DISPLAY DEVICE CONTAINING THE BENZO DIHETEROCYCLIC COMPOUND

(71) Applicant: WuHan TianMa Micro-Electronics Co., Ltd., Wuhan (CN)

(72) Inventors: Wei Gao, Wuhan (CN); Lei Zhang, Wuhan (CN); Qing Zhu, Wuhan (CN); Jinghua Niu, Wuhan (CN); Ping An, Wuhan (CN); Gaojun Huang, Wuhan (CN)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 523 days.

(21) Appl. No.: 16/243,372

(22) Filed: Jan. 9, 2019

(65) Prior Publication Data

US 2020/0106044 A1    Apr. 2, 2020

(30) Foreign Application Priority Data

Sep. 29, 2018 (CN) .......................... 201811147932.3

(51) Int. Cl.
*H01L 51/50* (2006.01)
*H01L 51/52* (2006.01)
(Continued)

(52) U.S. Cl.
CPC ........ *H01L 51/5253* (2013.01); *C07D 495/04* (2013.01); *C09K 11/06* (2013.01);
(Continued)

(58) Field of Classification Search
None
See application file for complete search history.

(56) References Cited

U.S. PATENT DOCUMENTS

| 2011/0049477 A1 | 3/2011 | Meng |
| 2017/0069850 A1 | 3/2017 | Hwang et al. |

FOREIGN PATENT DOCUMENTS

| CN | 109096246 A | 12/2018 |
| CN | 109096279 A | 12/2018 |

(Continued)

OTHER PUBLICATIONS

CN Office Action dated Oct. 21, 2019 for corresponding CN Application No. 201811147932.3.

*Primary Examiner* — Gregory D Clark
(74) *Attorney, Agent, or Firm* — Tarolli, Sundheim, Covell & Tummino LLP

(57) ABSTRACT

The present disclosure provides a benzo diheterocyclic compound having a structure represented by Formula (I). In Formula (I), $Y_1$ and $Y_2$ are oxygen or sulfur; $Ar_1$ and $Ar_2$ are each independently selected from a group consisting of single bond, a substituted or unsubstituted phenyl, a substituted or unsubstituted naphthyl, a substituted or unsubstituted anthracyl, a substituted or unsubstituted phenanthryl, a substituted or unsubstituted acenaphthylenyl, and a substituted or unsubstituted aromatic heterocyclic group; m and n are integers independently selected from 0 and 1; $D_1$ and $D_2$ are aryl or heteroaryl, $Ar_3$ and $Ar_4$ are aryl or heteroaryl, and $R_1$ is hydrogen, phenyl, or naphthyl. When the benzo diheterocyclic compound is used as a capping layer of a cathode, it will not interfere light emission of an OLED, and the OLED can maintain a high color purity.

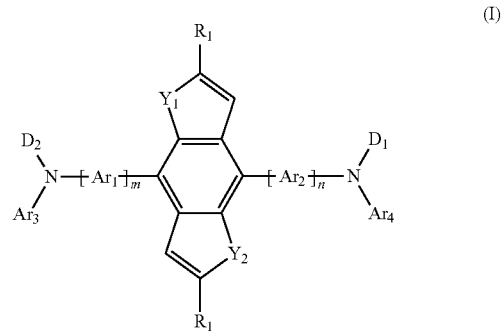

20 Claims, 2 Drawing Sheets

(51) Int. Cl.
*C07D 495/04* (2006.01)
*C09K 11/06* (2006.01)
*H01L 51/00* (2006.01)

(52) U.S. Cl.
CPC .. *H01L 51/0061* (2013.01); *C09K 2211/1018* (2013.01); *H01L 51/0072* (2013.01); *H01L 51/0074* (2013.01); *H01L 51/5012* (2013.01); *H01L 51/5056* (2013.01); *H01L 51/5064* (2013.01); *H01L 51/5072* (2013.01); *H01L 51/5088* (2013.01); *H01L 51/5092* (2013.01); *H01L 51/5096* (2013.01); *H01L 2251/558* (2013.01)

(56) References Cited

FOREIGN PATENT DOCUMENTS

| | | |
|---|---|---|
| CN | 109293645 A | 2/2019 |
| JP | 10-340786 | 12/1998 |

BENZO DIHETEROCYCLIC COMPOUND, DISPLAY PANEL, AND DISPLAY DEVICE CONTAINING THE BENZO DIHETEROCYCLIC COMPOUND

CROSS-REFERENCE TO RELATED APPLICATIONS

The present application claims priority to Chinese Patent Application No. 201811147932.3, filed on Sep. 29, 2018, the content of which is incorporated herein by reference in its entirety.

TECHNICAL FIELD

The present disclosure relates to the technical field of organic electroluminescent materials, and particularly, to a benzo diheterocyclic compound, a display panel and a display device containing the benzo diheterocyclic compound.

BACKGROUND

According to a direction of light emitted from an organic light-emitting layer, organic light-emitting diode (OLED) display devices can be classified into a bottom emission-type OLED display device and a top emission-type OLED display device. In the bottom emission-type OLED display device, light is emitted toward a substrate, a reflection electrode is formed above the organic light-emitting layer, and a transparent electrode is formed below the organic light-emitting layer. If the OLED display device is an active matrix OLED display device, a part of thin film transistors formed therein does not transmit light, resulting in a decrease of light-emitting area. In the top emission-type OLED display device, the transparent electrode is formed above the organic light-emitting layer, and the reflection electrode is formed below the organic light-emitting layer, so that the light is emitted in a direction opposite to the substrate, thereby increasing the light transmission area and brightness.

In order to improve luminescence efficiency, several common methods are known, for example forming folds, photonic crystals, or microlens arrays (MLA) on a surface of the substrate from which light is emitted, coating a covering layer having high refractive index on a transflective electrode having low refractive index, etc. In the case of forming folds or photonic crystals on the surface of the substrate from which light is emitted, an angle distribution of a radiation spectrum of the OLED is affected. In the case of forming a microlens array on the surface of the substrate from which light is emitted, the manufacturing process is complex. On the contrary, the process of coating the covering layer is relatively simple and can significantly improve the luminescence efficiency, and thus gains interest in recent years.

At present, methods for improving performance of the OLED components include: lowering a driving voltage, improving the luminescence efficiency, and prolonging a service life of the devices. In order to continuously improve the performance of the OLED components, it is urgent to innovate not only the structure and manufacturing process of the OLED components, but also electroluminescent materials used in the OLED components.

During a preparation of OLED components by means of vapor deposition, a high-precision metal mask is required to form a covering layer. However, a thermal deformation of the metal mask may lead to a poor positioning accuracy. That is, a melting point of ZnSe is higher than 1100° C. (Appl. Phys. Lett., 2003, 82, 466), and the high-precision mask cannot be accurately deposited onto a specific position. At the same time, inorganic materials are mostly evaporated at high temperature and thus are not suitable for the use of the high-precision mask. An inorganic material film-forming method based on sputtering also causes damage to light-emitting devices, so that the inorganic materials cannot be used to form the covering layer.

In view of a low efficiency in light extraction of OLED components, a capping layer (CPL, also referred as to a cathode covering layer), i.e., a light extraction material, is required to cover a surface of the cathode in the top emission-type device, in order to adjust an optical interference distance, suppress external light emission, and suppress the extinction caused by a movement of surface plasma. Based on principles of optical absorption and refraction, a higher refractive index of the material of such surface covering layer is conducive.

The materials of the cathode covering layer are classified into an inorganic type and an organic type. At present, the materials of CPL are mainly hole transmission-type materials and electron transmission-type materials. An example of the organic light-emitting layer (EL) material known in the prior art is 8-hydroxyquinoline aluminum (hereinafter referred to as Alq3), which is usually used as a green light-emitting material or an electron transmission material. When Alq3 is applied in the cathode covering layer for adjusting the refractive index, it has weak absorption of light having a wavelength near 450 nm emitted by a blue light-emitting device. Therefore, when Alq3 is applied to the blue light-emitting device, a problem of reduced color purity may occur.

The existing CPL materials have following problems: (1) insufficient refractive index and poor light extraction effect; and (2) large difference between the refractive indexes respectively measured in wavelength regions of blue light, green light and red light. Therefore, not all kinds of light can be extracted with a high light extraction efficiency in a light-emitting device that emits blue, green and red light at the same time. In this regards, it is urgent to develop a new CPL material having a refractive index as high as possible at respective wavelengths to improve the extraction efficiency with respect to light having different colors.

SUMMARY

In a first aspect, the present disclosure provides a benzo diheterocyclic compound having a structure represented by Formula (I):

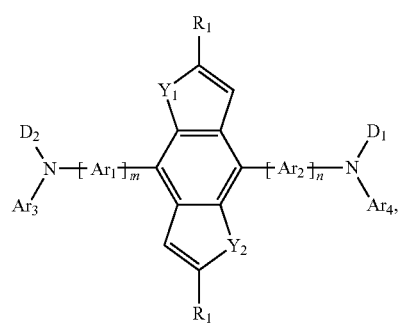

Formula (I)

in which Y1 and Y2 are each independently selected from oxygen or sulfur;

R1 is selected from a group consisting of hydrogen, phenyl, and naphthyl;

Ar1 and Ar2 are each independently selected from a group consisting of single bond, a substituted or unsubstituted phenyl, a substituted or unsubstituted naphthyl, a substituted or unsubstituted anthracyl, a substituted or unsubstituted phenanthryl, a substituted or unsubstituted acenaphthylenyl, and a substituted or unsubstituted aromatic heterocyclic group; m and n are integers independently selected from 0 and 1;

$D_1$ and $D_2$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, diarylamino, a diarylamine-derived group, triarylamino and a triarylamine-derived group; and Ar3 and Ar4 are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, and triarylamino and a triarylamine-derived group.

In a second aspect, the present disclosure provides a display panel including an organic light-emitting component. The organic light-emitting component includes an anode, a cathode, a light-emitting layer disposed between the anode and the cathode, and a capping layer covering the cathode. The capping layer includes one or more benzo diheterocyclic compounds according to the first aspect of the present disclosure.

In a third aspect, the present disclosure provides a display device including the display panel according to the second aspect of the present disclosure.

DESCRIPTION OF EMBODIMENTS

Figure 1:
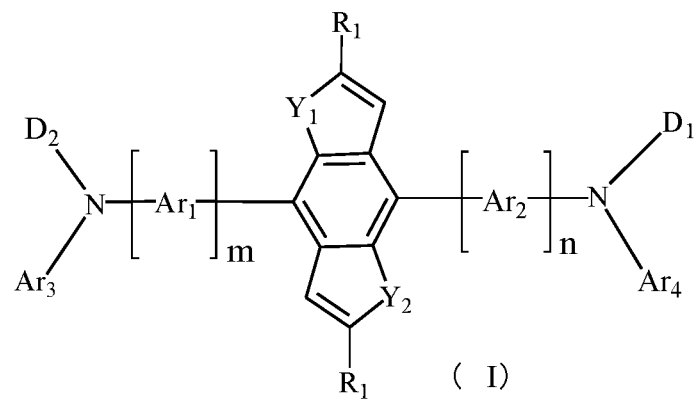
FIG. 1 is a chemical formula of a benzo diheterocyclic compound according to the present disclosure.

The present disclosure is described in detail with aid of embodiments and comparative examples. These embodiments are only used to illustrate the present disclosure, but not intended to limit the scope of the present disclosure. Without departing from the scope of the present disclosure, any modification or equivalent replacement with respect to the technical solutions of the present disclosure shall fall into the scope of protection of the present disclosure.

In a first aspect, the present disclosure provides a benzo diheterocyclic compound having a structure represented by Formula (I):

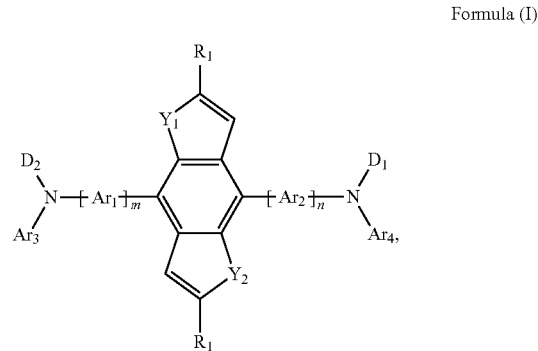

Formula (I)

in which $Y_1$ and $Y_2$ are each independently selected from oxygen or sulfur;

$R_1$ is selected from a group consisting of hydrogen, phenyl, and naphthyl;

$Ar_1$ and $Ar_2$ are each independently selected from a group consisting of single bond, a substituted or unsubstituted phenyl, a substituted or unsubstituted naphthyl, a substituted or unsubstituted anthracyl, a substituted or unsubstituted phenanthryl, a substituted or unsubstituted acenaphthylenyl, and a substituted or unsubstituted aromatic heterocyclic group; m and n are integers independently selected from 0 and 1; when m is 0, $(Ar_3)(D_2)N$— is bonded to the benzene ring in the Formula (I); and when n is 0, $(Ar_4)(D_1)N$— is bonded to the benzene ring in the Formula (I);

$D_1$ and $D_2$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, diarylamino, a diarylamine-derived group, triarylamino and a triarylamine-derived group; and $Ar_3$ and $Ar_4$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, diarylamino, a diarylamine-derived group, triarylamino and a triarylamine-derived group.

The present disclosure differs from the prior art in that the benzene ring of a benzo diheterocyclic ring is modified by incorporating a moiety of thiophene or furan, thereby effectively increasing the refractive index. However, since the moiety of thiophene or furan is not located in a main conjugate chain, it cannot expand the conjugation, and will not cause a red shift of the absorption spectrum of compound, so that the absorption of compound in the visible light region is less. When the benzo diheterocyclic compound according to the present application is used as the material of capping layer of the cathode, it will not interfere light-emitting of OLED, and thus the OLED can maintain a high color purity.

At least the following advantages can be obtained by applying the benzo diheterocyclic compound according to the present disclosure in the organic light-emitting components:

(1) the benzo diheterocyclic compound according to the present disclosure contains oxygen or sulfur element (especially sulfur element), and thus has a high polarizability, which is conducive to obtaining materials with high refractive index;

(2) the benzo diheterocyclic compound according to the present disclosure has unique electrical, optical, redox and self-assembly properties, a larger rigid conjugated system on a two-dimensional plane, and strong π-π interaction between molecules, and thus can achieve a more ordered molecular alignment and an improved light extraction efficiency, making it an important candidate for the capping layer material of the cathode;

(3) oxygen atom or sulfur atom has good polarizability and high electron-rich properties, and in this regard, this kind of the aromatic heterocyclic organic materials has good charge transfer and electron-donating properties.

Compared with the prior art, the present application brings at least the following beneficial effects:

(1) It is feasible that the small organic molecules that are suitable for vapor deposition are used as the capping layer material in the present disclosure; the capping material contains molecules having a benzo diheterocyclic ring structure, and thus has high refractive index and high film forming stability; further, the absorption region of the capping layer material is generally in the ultraviolet band, and thus has a small absorption coefficient for the visible light.

(2) The capping layer material used in the present disclosure has a gradually decreasing refractive index with respect to light in the wavelength range of 450-630 nm, and the refractive index difference between light in a high wavelength band and light in a low wavelength band is relatively small, i.e., the change of refractive index for the three colors R/G/B is insignificant, and in this regard, the influence of the capping layer material on the light extraction efficiency of the colors R/G/B is reduced. Therefore, the capping layer material has practicability in the display panel.

(3) The present disclosure can achieve good light transmittance by adopting a combination of the capping layer and the cathode, and thus can guarantee an integral light extraction efficiency of the device.

In an embodiment of the benzo diheterocyclic compound according to the present disclosure, the benzo diheterocyclic compound has the following structure:

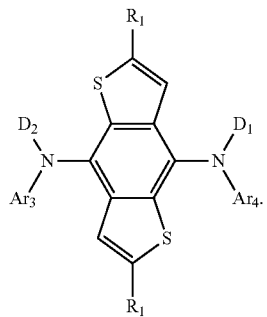

In an embodiment of the benzo diheterocyclic compound according to the present disclosure, the benzo diheterocyclic compound has the following structure:

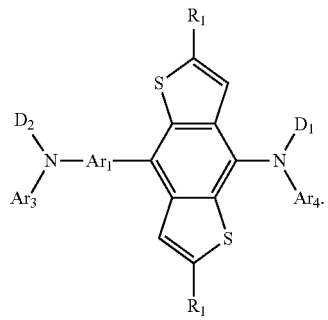

In an embodiment of the benzo diheterocyclic compound according to the present disclosure, the aromatic heterocyclic group is selected from a group consisting of thienyl, thiazolyl, thiadiazolyl, furyl, oxazolyl, and oxadiazolyl.

In an embodiment of the benzo diheterocyclic compound according to the present disclosure, $D_1$ and $D_2$ are each independently selected from a group consisting of a carbazole-derived group, an acridine-derived group, diarylamino, a diarylamine-derived group, triarylamino and a triarylamine-derived group. $Ar_3$ and $Ar_4$ are each independently selected from a group consisting of a substituted or unsubstituted phenyl, a substituted or unsubstituted biphenyl, a substituted or unsubstituted naphthyl, and a substituted or unsubstituted anthracyl.

A moiety of benzodithiophene (BDT) has a large rigid planar symmetric conjugate structure, which enhances delocalization ability of π electrons and π-π interaction of molecules. It is conducive to achieving higher molecular polarizability, compact molecular stacking of molecules, and reduced molecular volume, thereby increasing the refractive index. Besides, it is easy to chemically modify, synthesize and purify the moiety of benzodithiophene, and the moiety of benzodithiophene has high stability in air environment. The moiety of BDT can be modified by incorporating various substituents by means of chemical tailoring, so as to adjust a solubility and energy level of the whole molecule. Moreover, the moiety of BDT has a planar symmetric structure, which can effectively enhance the π-π stacking between molecular chains and thus achieves a higher mobility of holes.

The moiety of benzodithiophene has following advantages: (1) sulfur element included in the molecule has a high polarizability, which is conducive to obtaining a material with high refractive index; (2) unique electrical, optical, redox and self-assembly properties that can achieve more ordered alignment of molecule and thus results in an important candidate for organic electronics materials; (3) sulfur atom has good polarizability and high electron-rich property, so that this kind of aromatic heterocyclic organic materials have good performance of charge transferring and electron donating.

In an embodiment of the benzo diheterocyclic compound according to the present disclosure, the carbazole-derived group is selected from a group consisting of the following groups:

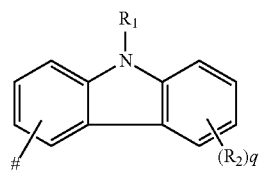
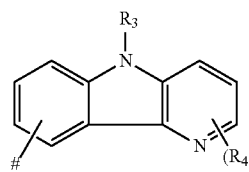

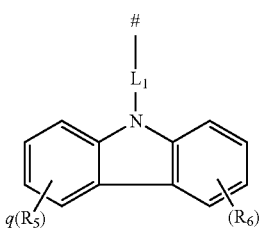
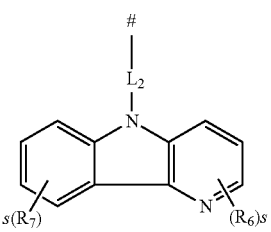

-continued

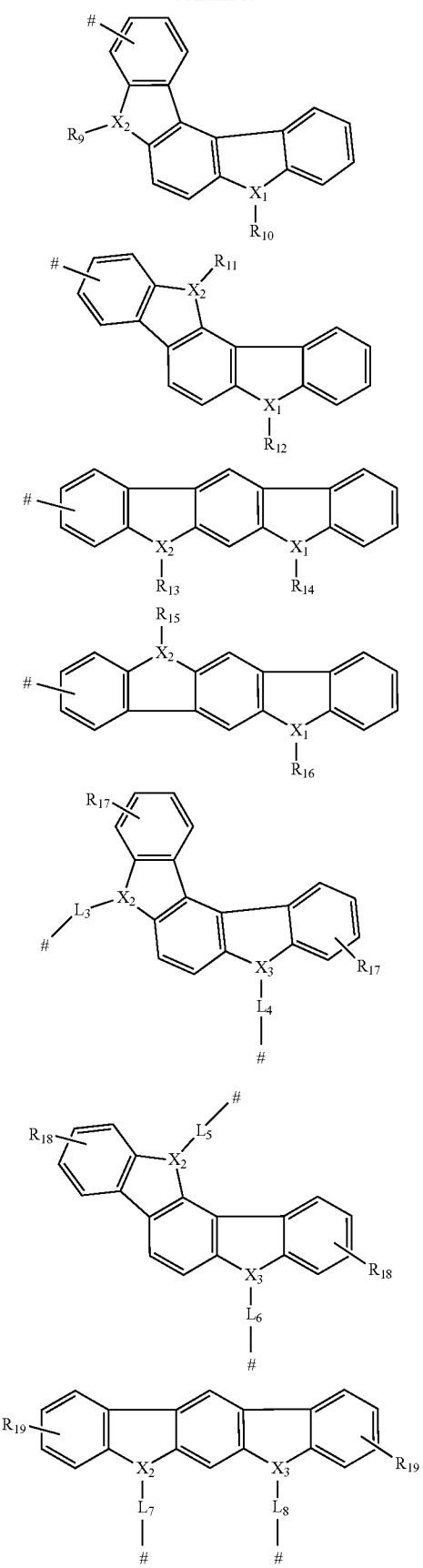

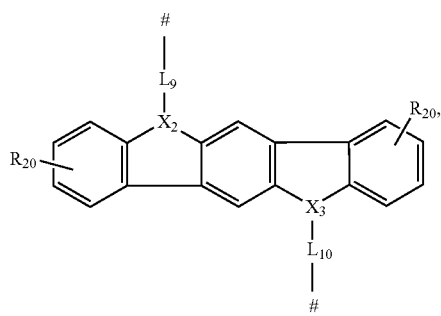

in which $X_1$, $X_2$, and $X_3$ are each independently selected from a group consisting of carbon, nitrogen, oxygen, sulfur, and silicon, and at least one of $X_1$, $X_2$, and $X_3$ is nitrogen;

$R_1$-$R_{20}$ are each independently selected from a group consisting of alkyl, alkoxy, an aromatic ring group, an aromatic fused ring group, and an aromatic heterocyclic group, and q and s are integers independently selected from 0, 1, 2, and 3;

$L_1$-$L_{10}$ are each independently selected from a group consisting of an aromatic ring group, an aromatic fused ring group, and an aromatic heterocyclic group; and # represents a bonding position.

In an embodiment of the benzo diheterocyclic compound according to the present disclosure, the aromatic ring group is phenyl; the aromatic fused ring group is selected from a group consisting of naphthyl, anthracyl, pyrenyl, and perylenyl; and the aromatic heterocyclic group is selected from a group consisting of thienyl, furyl, and thiazolyl.

In an embodiment of the benzo diheterocyclic compound according to the present disclosure, the carbazole-derived group is selected from a group consisting of the following groups:

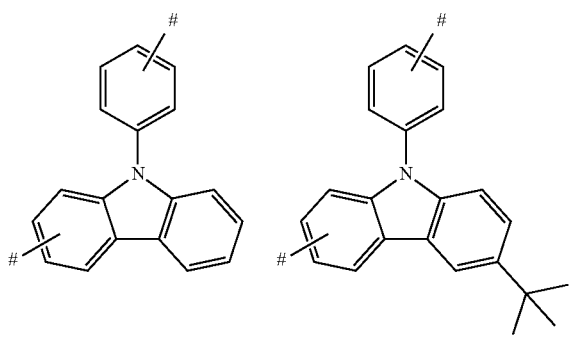

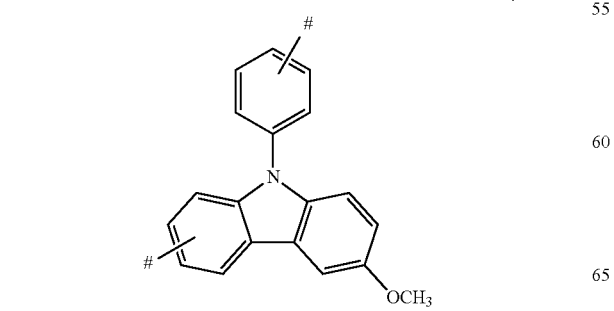

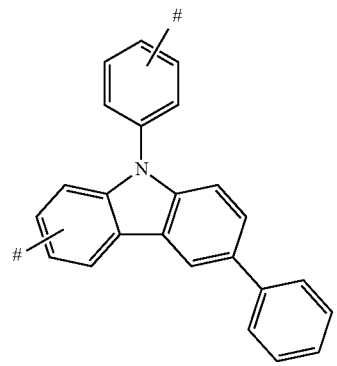

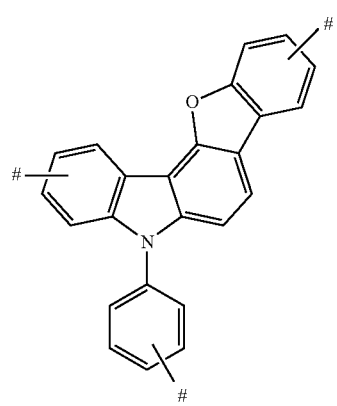

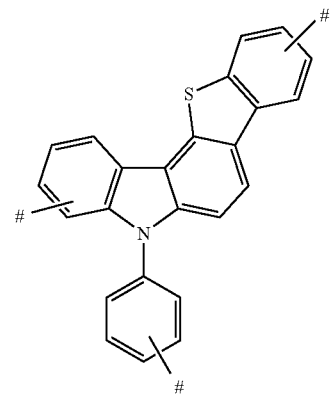

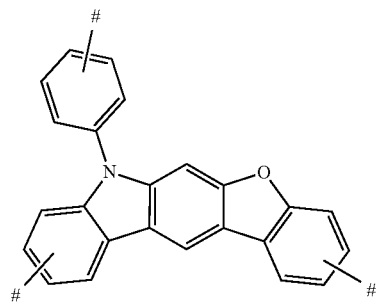

-continued
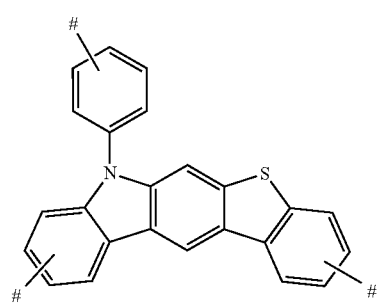
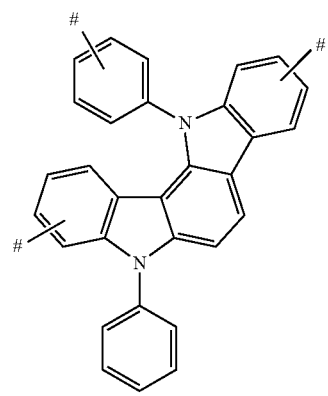
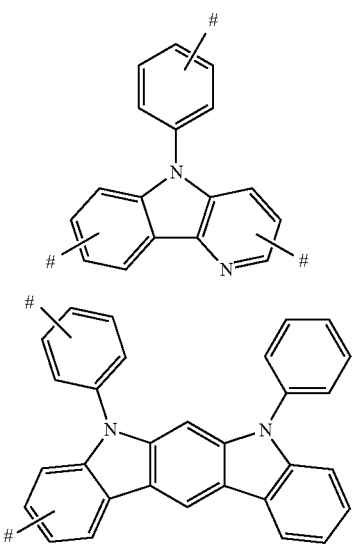
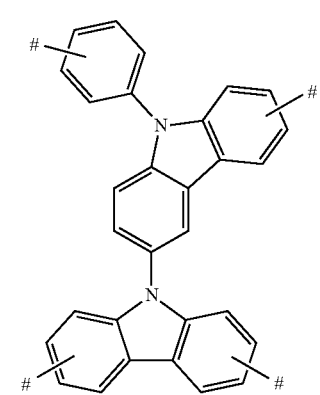
-continued
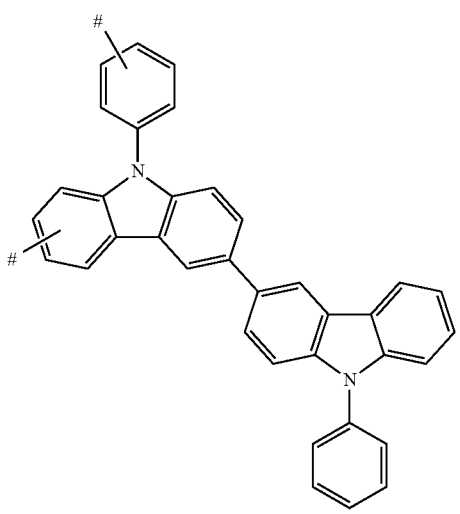
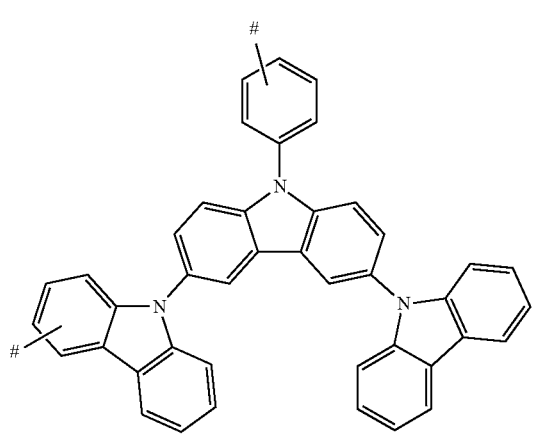
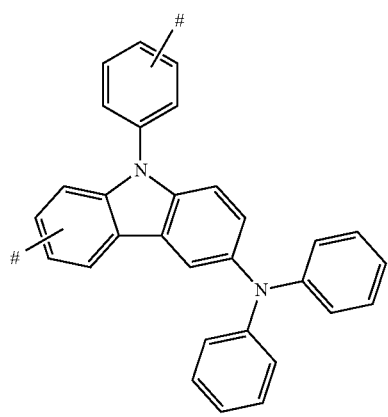

-continued

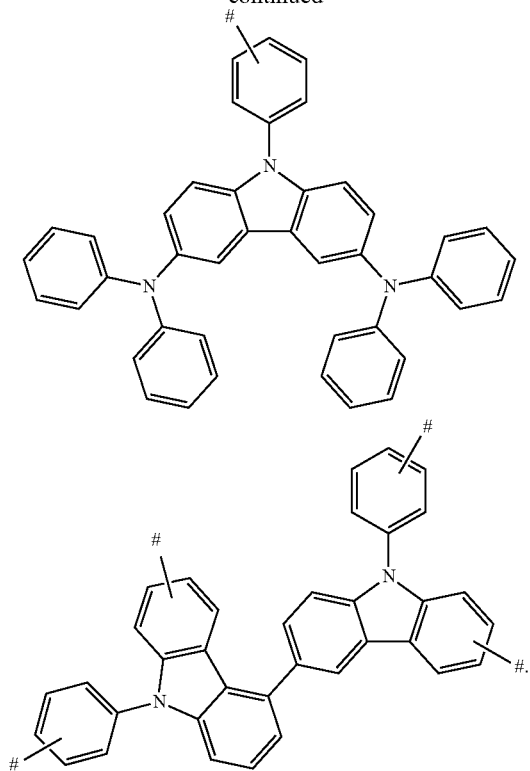

The carbazolyl, as an electron-donating group, can form a dipole-dipole interaction together with the central benzo diheterocyclic ring, which enhances polarizability and makes the compound according to the present disclosure have a higher refractive index. Carbazole can be evaporated in high vacuum to form an amorphous film without pinhole defects, which has better thermal, chemical, electrochemical and photochemical stability. Raw material is accessible, cheap, and easy to be synthesized.

In an embodiment of the benzo diheterocyclic compound according to the present disclosure, the acridine-derived group is selected from a group consisting of the following groups:

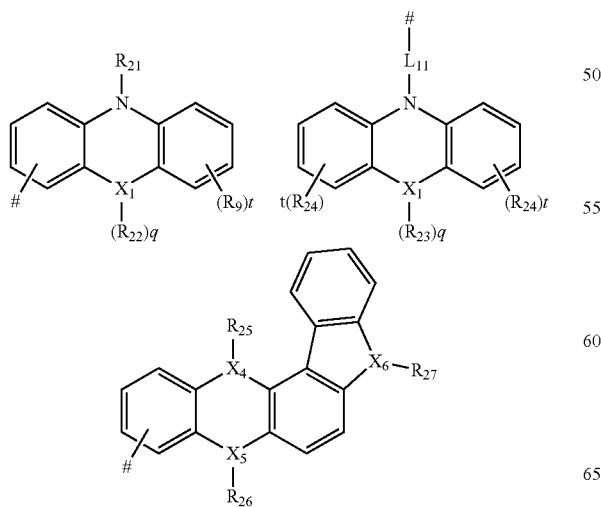

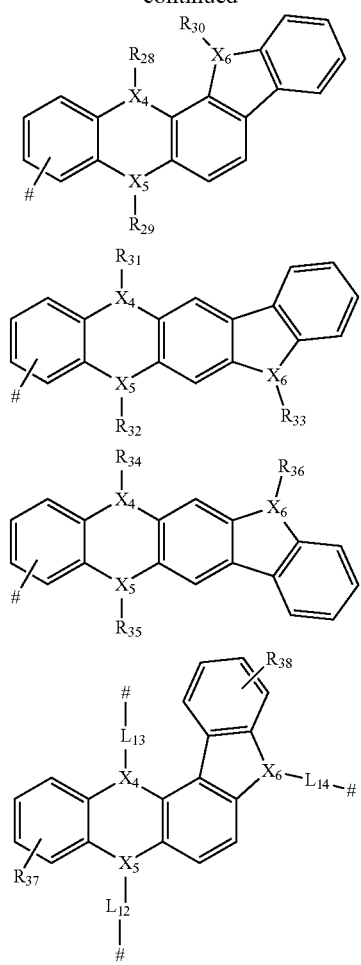

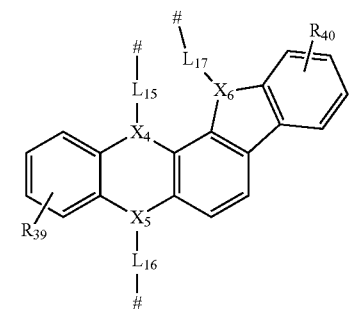

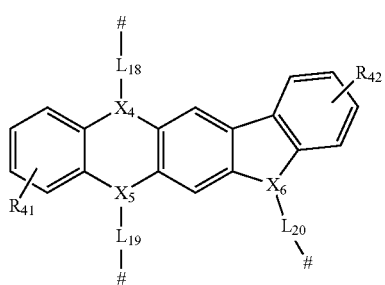

-continued

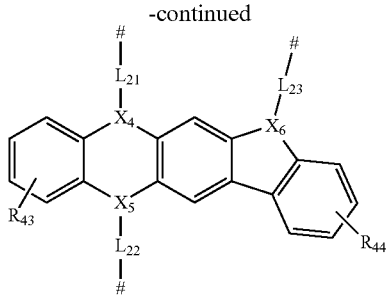

in which $X_1$, $X_4$, $X_5$, and $X_6$ are each independently selected from a group consisting of carbon, nitrogen, oxygen, sulfur, and silicon, and at least one of $X_4$ and $X_5$ is nitrogen;

$R_{21}$-$R_{44}$ are each independently selected from a group consisting of alkyl, alkoxy, an aromatic ring group, an aromatic fused ring group, and an aromatic heterocyclic group, and q and t are integers independently selected from 0, 1, 2, and 3;

$L_{11}$-$L_{23}$ are each independently selected from a group consisting of an aromatic ring group, an aromatic fused ring group, and an aromatic heterocyclic group; and # represents a bonding position.

In an embodiment of the benzo diheterocyclic compound according to the present disclosure, the acridine-derived group is selected from a group consisting of the following groups:

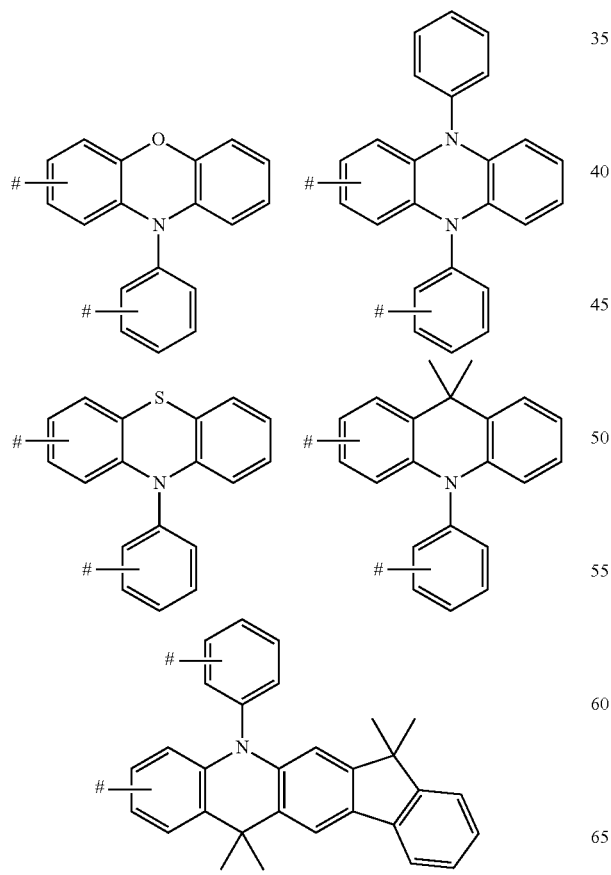

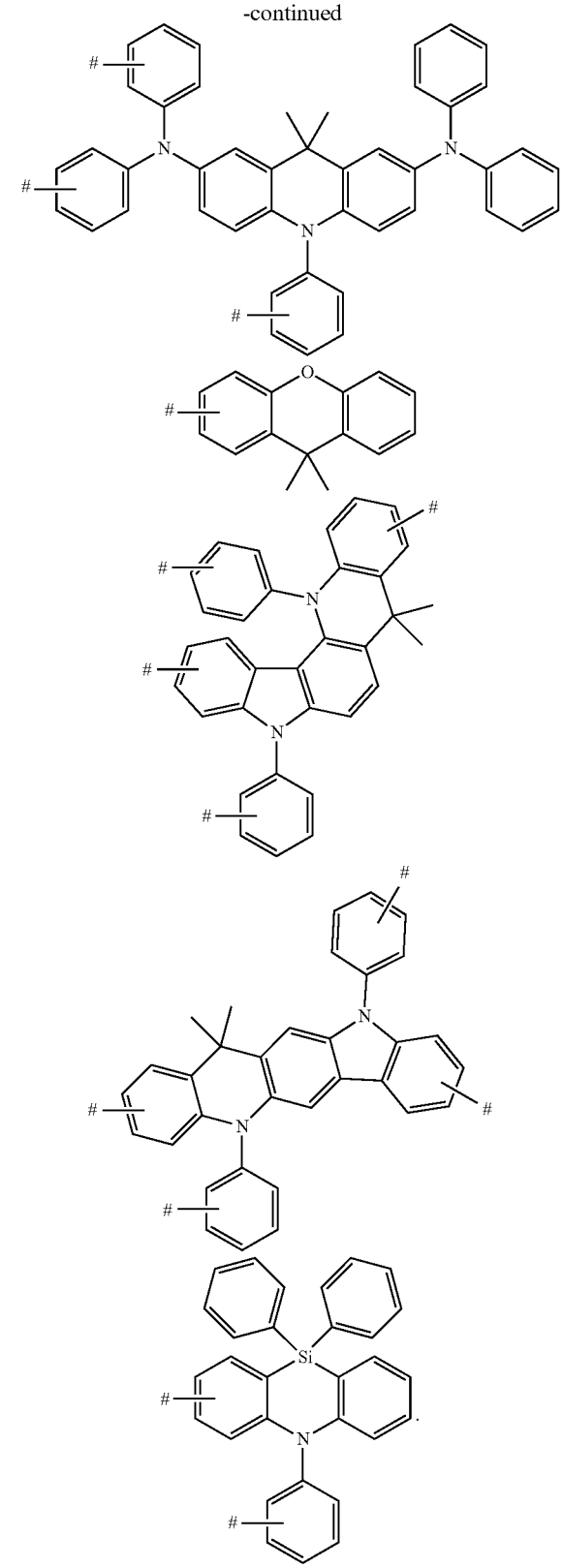

The acridine-derived groups are stronger electron-donating groups than the carbazole-derived groups. The acridine-derived groups can form stronger dipole-dipole interaction together with the central benzo diheterocyclic ring, which further enhances the polarizability and makes the compound according to the present disclosure have a higher refractive index. The N atom on the acridine-derived group is in an sp3 hybrid state, and has a non-planar structure, which is conducive to forming a uniform amorphous film by vapor deposition. At the same time, the acridine-derived group has a plurality of linkable sites, facilitating a chemical modification.

In an embodiment of the benzo diheterocyclic compound according to the present disclosure, diarylamino, the diarylamine-derived group, triarylamino or the triarylamine-derived group is selected from a group consisting of the following groups:

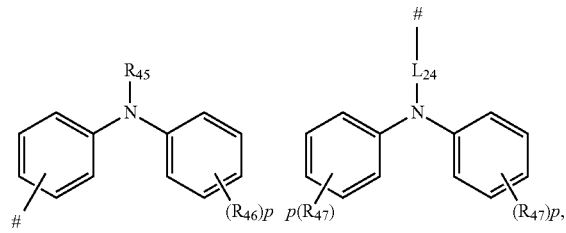

in which $R_{45}$-$R_{47}$ are each independently selected from a group consisting of alkyl, alkoxy, an aromatic ring group, an aromatic fused ring group, and an aromatic heterocyclic group, and p is an integer selected from 0, 1, 2, and 3;

$L_{24}$ is selected from a group consisting of an aromatic ring group, an aromatic fused ring group, and an aromatic heterocyclic group; and \# represents a bonding position.

In an embodiment of the benzo diheterocyclic compound according to the present disclosure, diarylamino, the diarylamine-derived group, triarylamino, or the triarylamine-derived group is selected from a group consisting of the following groups:

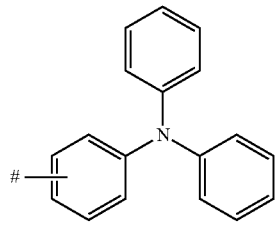

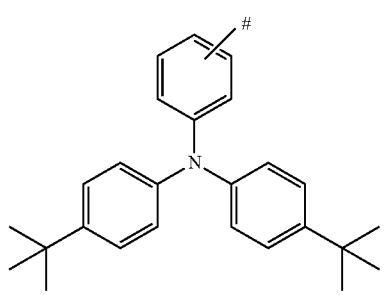

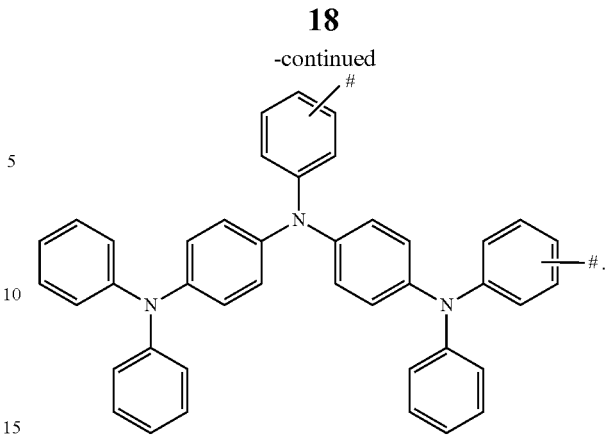

Aromatic amine-derived groups have following advantages: (1) the aromatic amine-derived groups are typical electron-donating groups with moderate electron-donating property, and can form strong dipole-dipole interaction together with the central benzo diheterocyclic ring, which enhances the polarizability and makes the compound according to the present disclosure have a high refractive index; (2) the aromatic amine-derived groups have good thermal, electrochemical and photochemical stability; the aromatic amine-derived material is accessible, cheap, and easy to be chemically modified; (3) N atom on the aromatic amine-derived group is in sp3 hybrid state, and has a non-planar structure, which is conducive to forming a uniform amorphous film.

In an embodiment of the benzo diheterocyclic compound according to the present disclosure, D1 and D2 are each independently selected from a group consisting of the following groups:

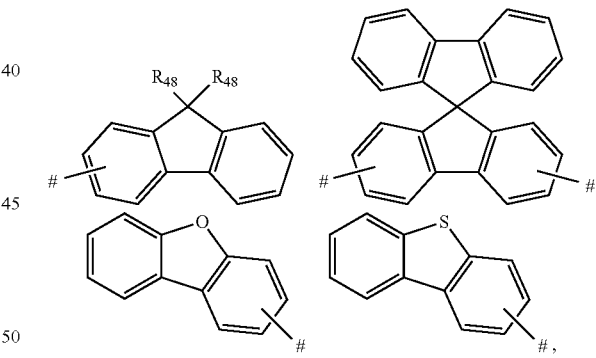

in which $R_{48}$ is selected from a group consisting of alkyl, alkoxy, an aromatic ring group, an aromatic fused ring group, and an aromatic heterocyclic group.

Fluorenyl has following advantages: (1) fluorenyl has a rigid planar structure, sites 2, 7 and 9 on the fluorenyl are accessible to chemical modification, such as incorporating various functional groups, for modifying physical and chemical properties, such as optical, electrical and processing properties of the molecules; (2) fluorenyl has a weak absorption in the visible light region, and is suitable to be the material of the capping layer; (3) fluorenyl has high thermal, electrochemical and photochemical stability; (4) the material of fluorenyl is cheap and easy to get.

Spirodifluorenyl bridges two fluorene monomers with a carbon atom in an sp3 hybrid state as the center, such that the two fluorene monomers have a non-planar spatial orthogonal structure, which can avoid a compact stacking of molecules and the formation of aggregates in the film. It is conducive to forming more stable and uniform amorphous film structure and improving the thermal stability of the material, thereby effectively increasing the glass transition temperature of the material, and inhibiting molecular crystallization. In this way, a more stable amorphous material can be obtained. The spatial orthogonal structure is also conducive to improving the solubility of the compound and facilitating solution processing. The structure of spirodifluorenyl has many reactive sites that can be chemically modified, and thus is also conducive to expanding a three-dimensional topological structure.

In an embodiment of the benzo diheterocyclic compound according to the present disclosure, the benzo diheterocyclic compound is selected from a group consisting of the following compounds:

P1
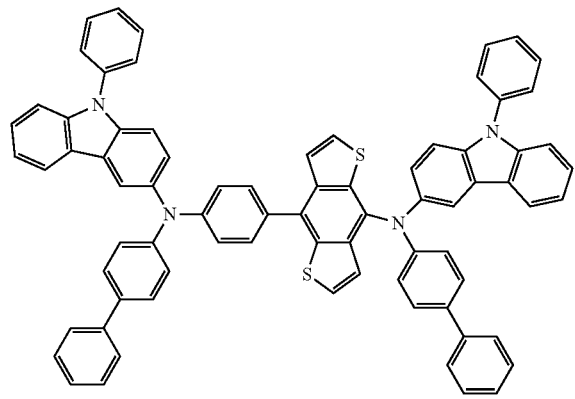

P2
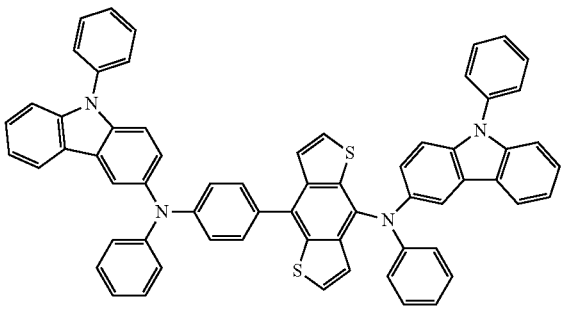

P3
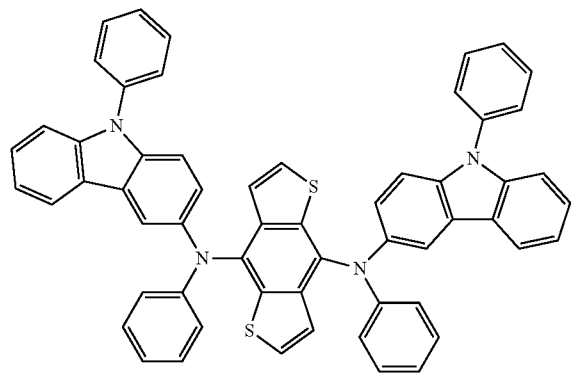

P4
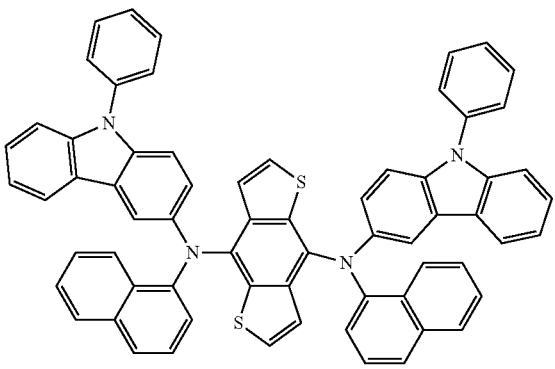

P5
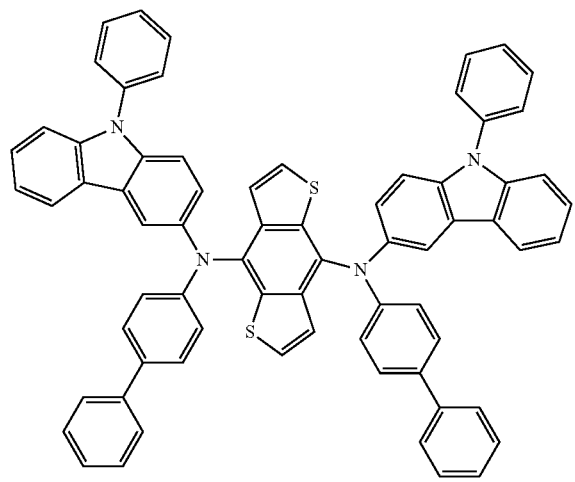

P6
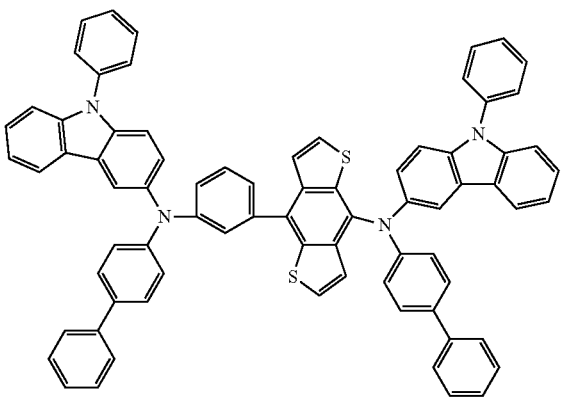

-continued
P7
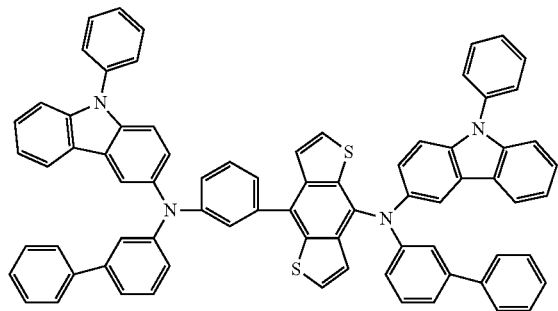
P8
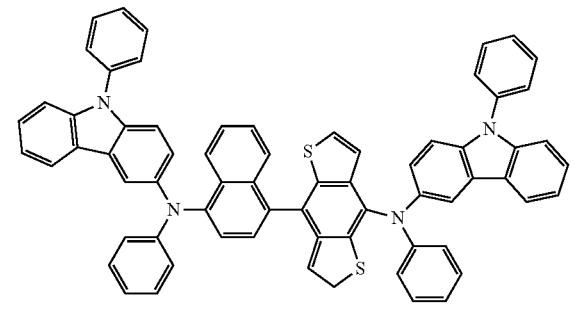
P9
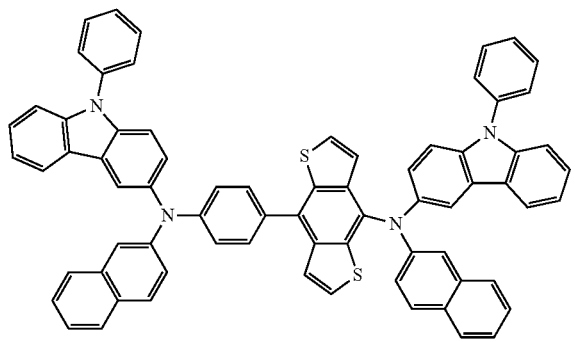
P10
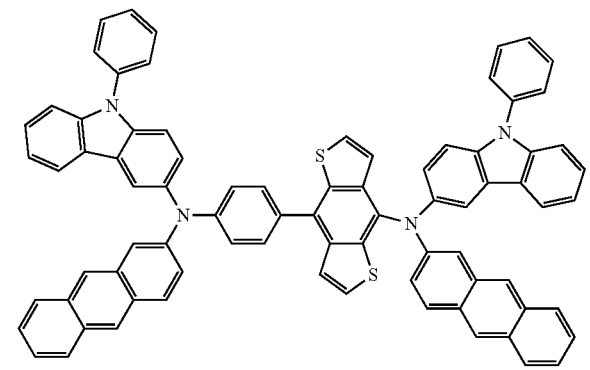
P11
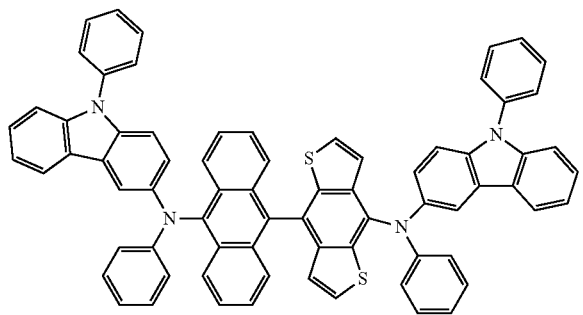
P12
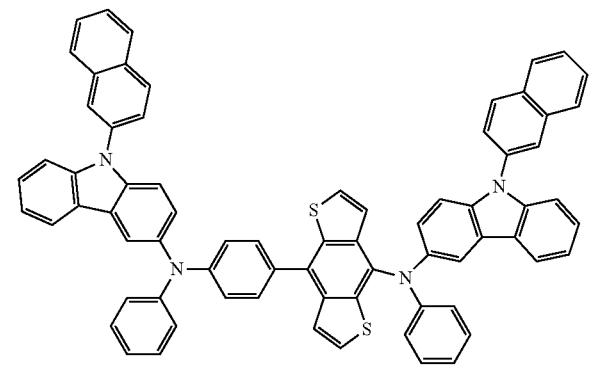
P13
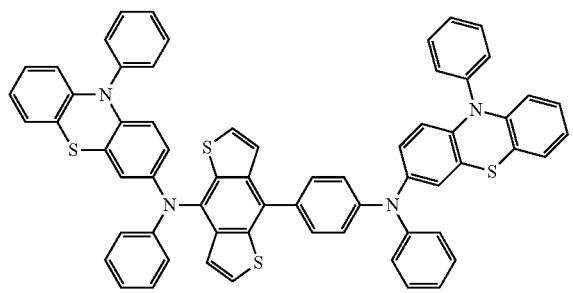
P14
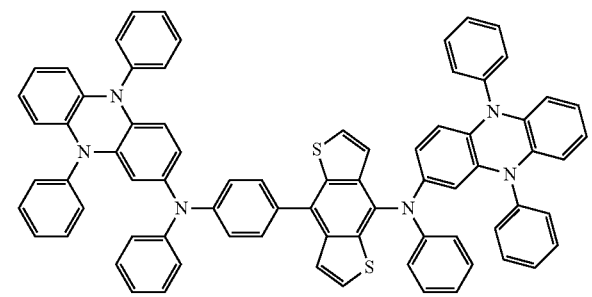

-continued
P15
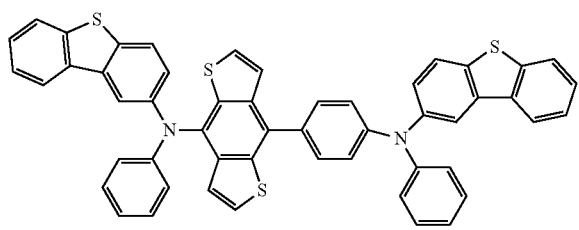
P16
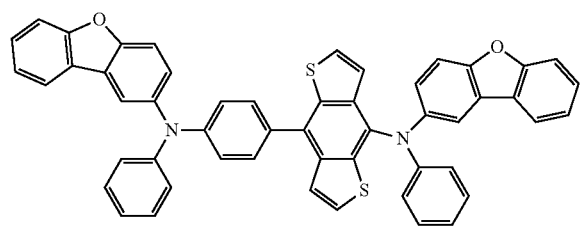
P17
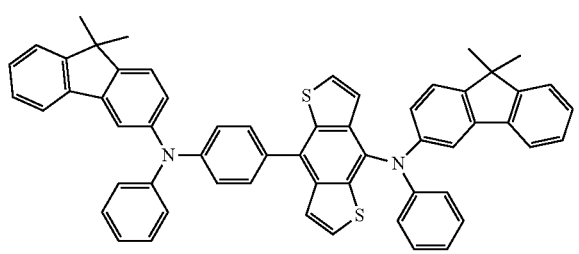
P18
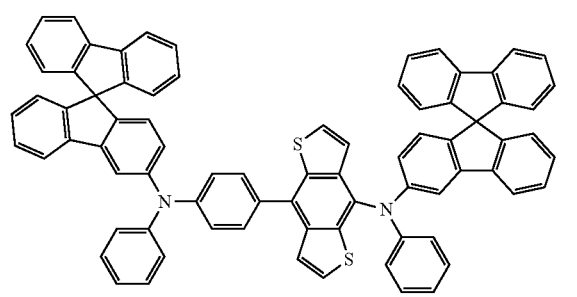
P19
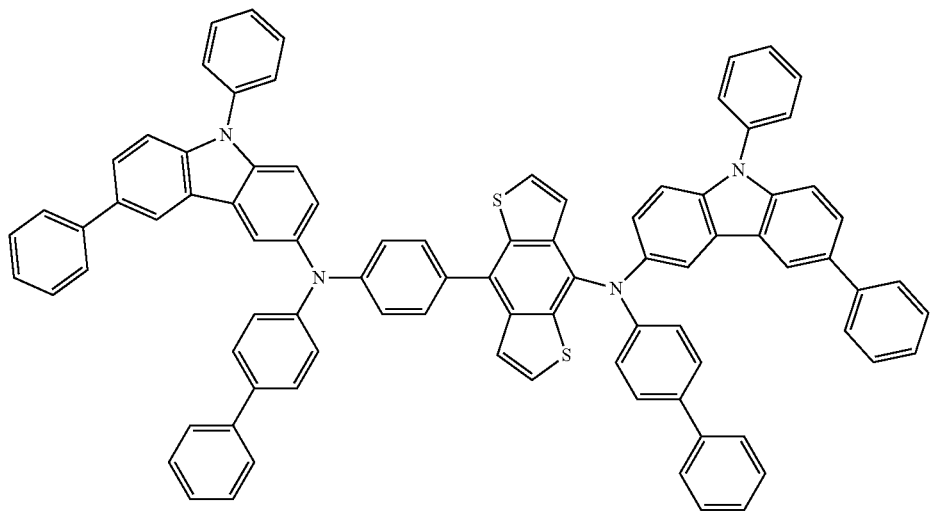
P20
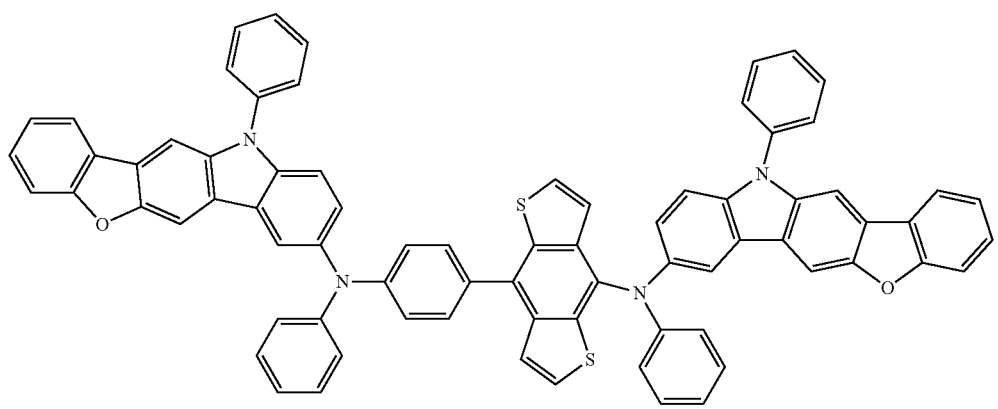

-continued
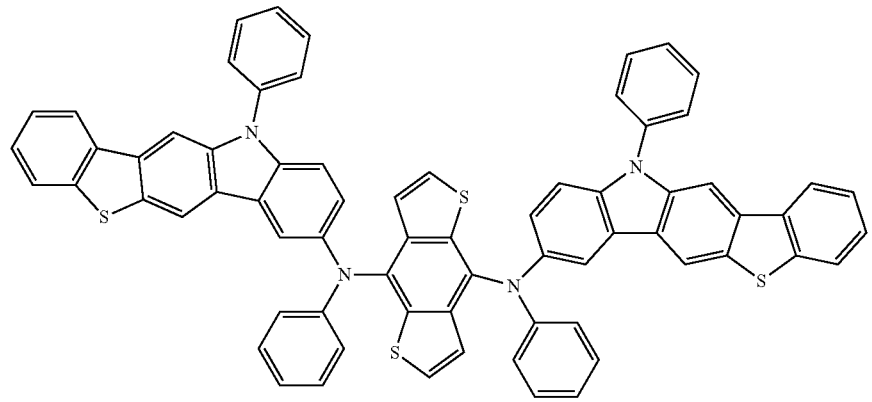
P21
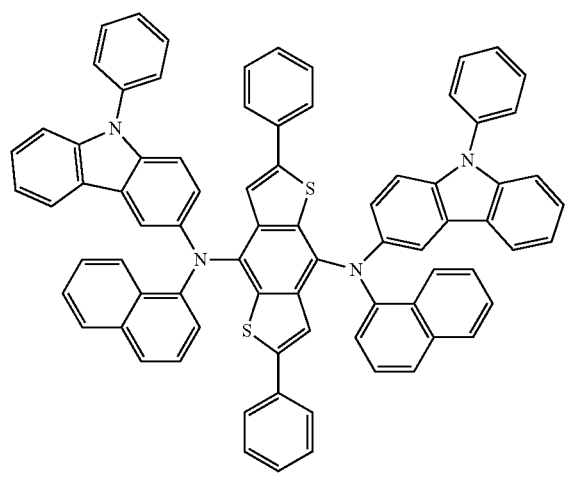
P22
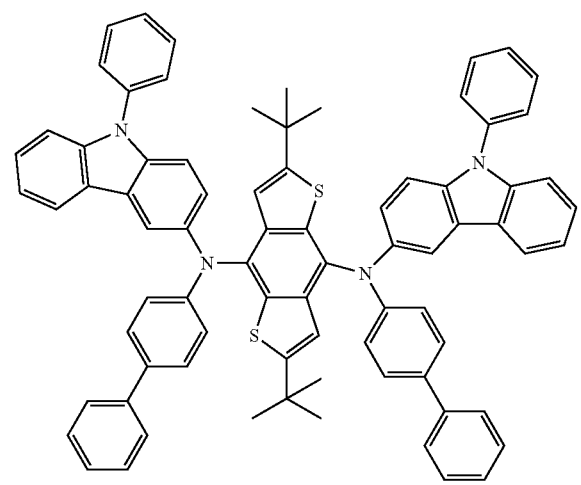
P23
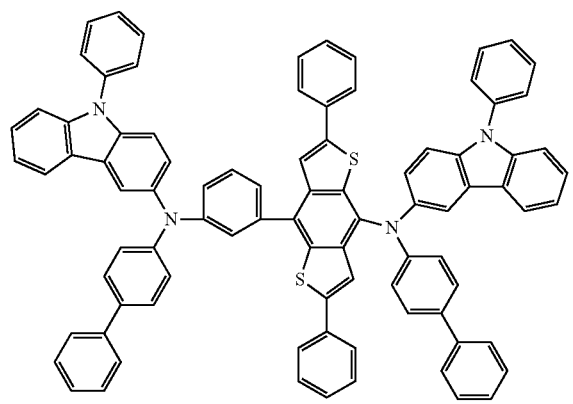
P24
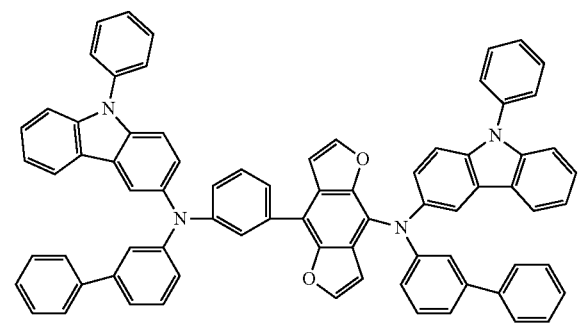
P25

-continued
P26
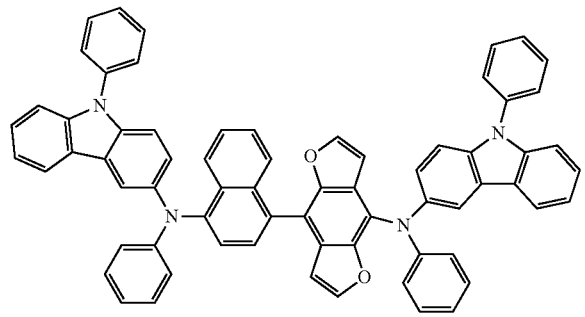
P27
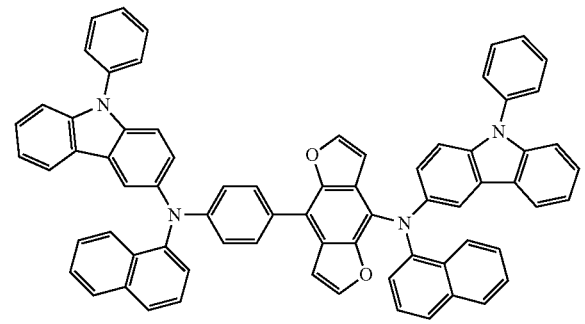
P28
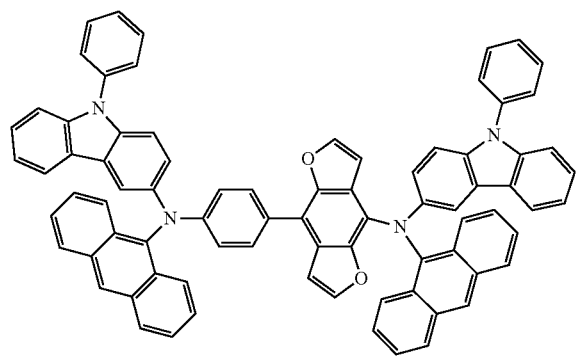
P29
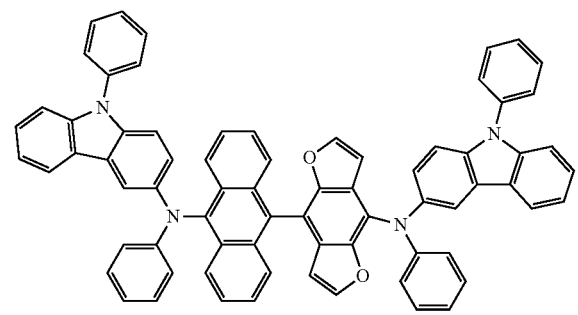
P30
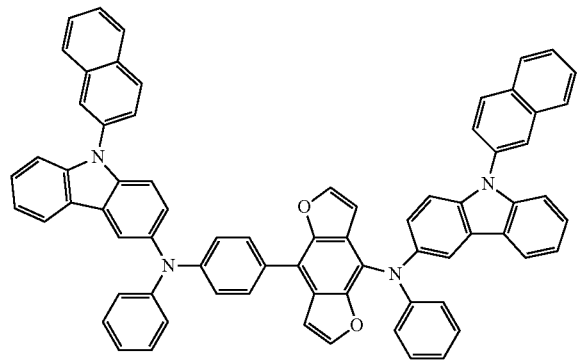
P31
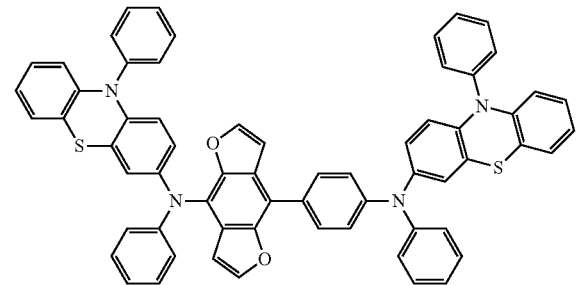
P32
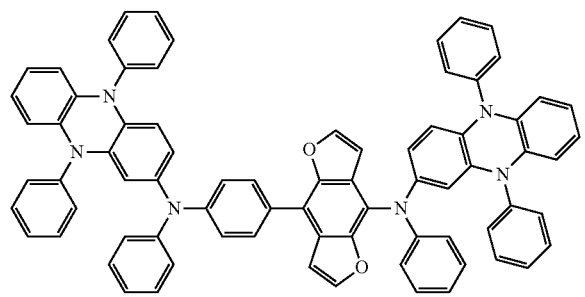
P33
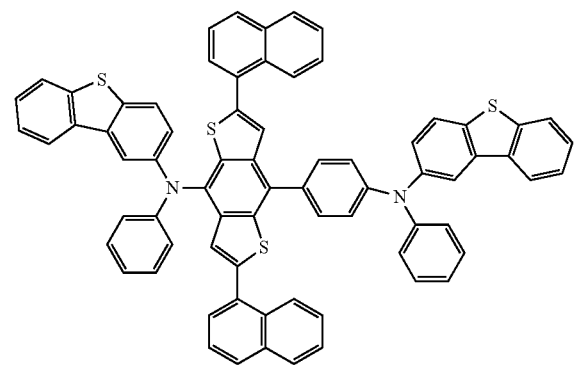

-continued

P34
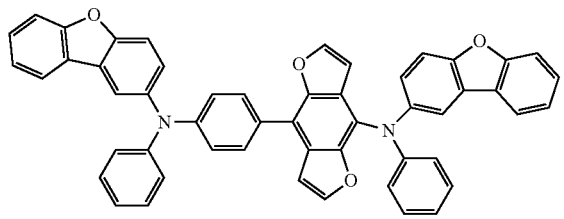

P35
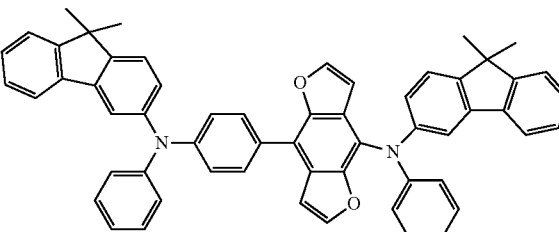

P36
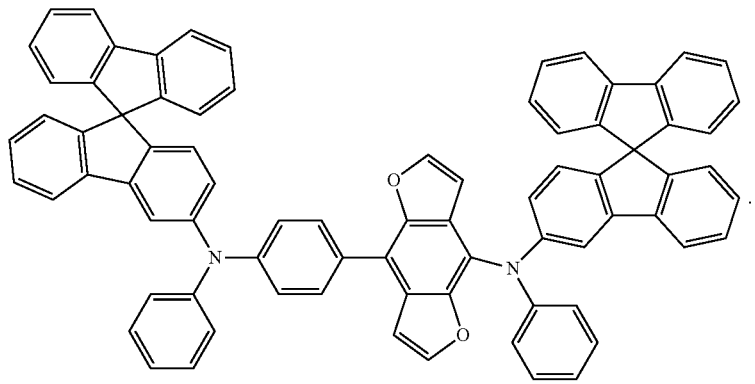

For a visible light having wavelength of 450 nm-630 nm, the benzo diheterocyclic compound according to the present disclosure has a refractive index of 1.85-2.50 and a light extinction coefficient less than 0.1. A difference between refractive indexes of the benzo diheterocyclic compound for a visible light of 450 nm and a visible light of 550 nm is smaller than 0.35; and a difference between refractive indexes of the benzo diheterocyclic compound for the visible light of 550 nm and a visible light of 630 nm is smaller than 0.15.

The material used for the capping layer (CPL) according to the present disclosure has a refractive index decreasing with wavelength in a range of 450-630 nm, and also has a small difference between the refractive indexes for light in a long-wavelength range and light in a short-wavelength range. That is, the refractive indexes for the three colors R/G/B alter in a small range, thereby reducing adverse influence on light extraction efficiency of light having different colors R/G/B. Thus, the material has strong practicability on the optical display panel.

Another aspect of the present disclosure provides an organic light-emitting display panel 11. The organic light-emitting display panel 11 includes an organic light-emitting component. The organic light-emitting component includes an anode 2, a cathode 9, a light-emitting layer 6 positioned between the anode 2 and the cathode 9, and a capping layer (CPL) 10 covering the cathode. The capping layer 10 includes one or more benzo diheterocyclic compounds according to the present disclosure.

In an embodiment of the organic light-emitting display panel according to the present disclosure, the capping layer (CPL) has a thickness of 30 nm-100 nm.

In an embodiment of the organic light-emitting display panel according to the present disclosure, a transmittance of the cathode together with the capping layer (CPL) for a visible light of 450-630 nm is greater than 65%.

In an embodiment of the organic light-emitting display panel according to the present disclosure, the organic light-emitting component further includes one or more of a hole injection layer, a hole transmission layer, an electron blocking layer, a hole blocking layer, an electron transmission layer, and an electron injection layer.

In an embodiment of the organic light-emitting display panel according to the present disclosure, the organic light-emitting component further includes a hole transmission layer, and the hole transmission layer includes one or more benzo diheterocyclic compounds according to the present disclosure.

In an embodiment of the organic light-emitting display panel according to the present disclosure, the organic light-emitting component further includes an auxiliary hole transmission layer positioned between the light-emitting layer and the hole transmission layer, and the auxiliary hole transmission layer is configured to control a resonant period of light emitted from the light-emitting layer.

In an embodiment of the organic light-emitting display panel according to the present disclosure, the light-emitting layer includes one or more benzo diheterocyclic compounds of the present disclosure.

In an organic light-emitting component provided by the present disclosure, the anode is made of metals such as copper, gold, silver, iron, chromium, nickel, manganese, palladium, platinum, or alloys thereof. The anode can also be made of metal oxides, for example, indium oxide, zinc oxide, indium tin oxide (ITO), indium zinc oxide (IZO), etc. The anode can also be made of conductive polymer such as polyaniline, polypyrrole, poly (3-methylthiophene), or the like. In addition to the anode material mentioned above, the anode also can be made of any suitable material selected from the anode materials known in the related art, and combinations thereof, as long as the material of the anode is conductive to injecting holes.

In the organic light-emitting component according to the present disclosure, the cathode can be made of metals such as aluminum, magnesium, silver, indium, tin, titanium, and alloys thereof. The cathode can also be made of multiplelayer metal material, such as LiF/Al, LiO₂/Al, BaF₂/Al, and the like. In addition to the cathode materials listed above, the cathode also can be made of any suitable material selected from the cathode material known in the related art, and combinations thereof, as long as the material of the cathode is conductive to injecting holes.

In the present disclosure, the organic light-emitting component can be prepared as follows: an anode is formed on a smooth transparent or opaque substrate, a thin organic layer is formed on the anode, and a cathode is formed on the thin organic layer. The thin organic layer can be formed by a known film forming method, for example, vapor deposition, sputtering, spin coating, dipping, ion plating, etc. Finally, an organic capping layer (CPL) is formed on the cathode. The CPL is made of a benzo diheterocyclic compound according to the present disclosure. The capping layer (CPL) can be prepared by vapor deposition or a solution processing method. The solution processing method includes ink-jet printing, spin coating, blade coating, screen printing, roll-to-roll printing, and the like.

In another aspect, the present disclosure provides several illustrative methods for preparing the benzo diheterocyclic compound according to the present disclosure, as described in the following Examples 1-5.

Example 1

Synthesis of Compound P1:

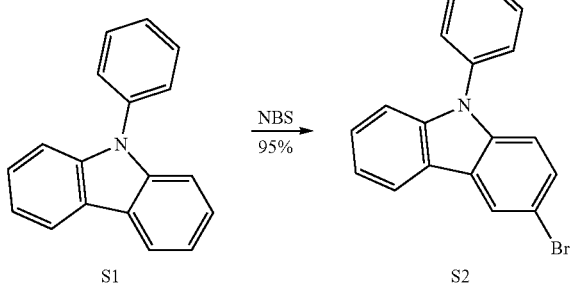

Compound S1 (10.0 mmol) was added to a two-necked flask (100 mL) and then 30 mL toluene degassed with nitrogen was added to dissolve the Compound S1. One of the two necks of the flask was connected to a constant pressure dropping funnel, and gas in the reaction system was replaced by nitrogen. N-bromosuccimide (NBS) was weighed (10.5 mmol) and dissolved by adding 20 mL toluene, then the toluene solution of NBS was added dropwise to the toluene solution of the Compound S1 through the dropping funnel at 0° C. and in dark place. After stirring for 2 hours, the temperature of the reaction system was slowly raised to room temperature and stirred overnight. 50 mL deionized water was added to quench the reaction, the mixture was extracted by dichloromethane (100 mL×3), following by collecting the organic phases of extraction and drying with anhydrous Na₂SO₄. The dried organic phase was then filtered and distilled at vacuum by using a rotary evaporator, so as to remove solvent and obtain a crude product. The crude product was purified by gradient elution through silica gel column chromatography to obtain solid powder S2 (9.5 mol, 95%).

MALDI-TOF MS: C₁₈H₁₂BrN, m/z calculated value: 321.0; measured value: 321.2.

Calculated values from elemental analysis: C, 67.10; H, 3.75; Br, 24.80; N, 4.35; measured values: C, 67.12; H, 3.77; Br, 24.78; N, 4.33.

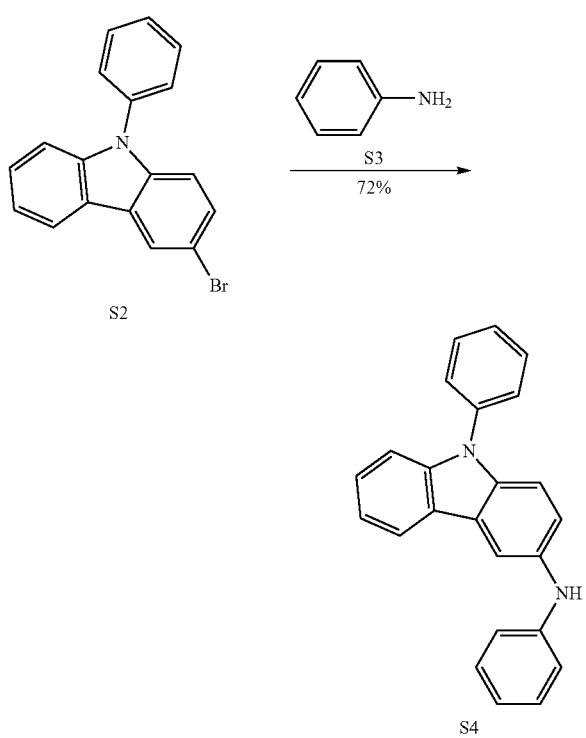

Compound S2 (10.0 mmol), Compound S3 (10.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was degased for 3 times while stirring, after nitrogen replacement, and 20 mL toluene was added by a syringe. The mixture was heated for reflux for 3 hours under a nitrogen stream, and then cooled to room temperature. After water was added in the cooled reaction solution, the mixture was extracted with dichloromethane, and washed with saturated salt water. The organic phase was dried with anhydrous sodium sulfate. The dried organic phase was then distilled to remove solvent and obtain a crude product. The crude product was purified by column chromatography to obtain an intermediate S4 (7.2 mmol, 72%).

MALDI-TOF MS: C₃₀H₂₂N₂S₄, m/z calculated value: 538.1; measured value: 538.4.

Calculated values from elemental analysis: C, 66.88; H, 4.12; N, 5.20; S, 23.81; measured value: C, 66.90; H, 4.15; N, 5.18; S, 23.78.

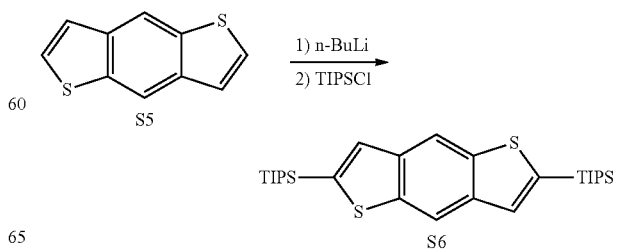

Under protection of nitrogen, Compound S5 (5 mmol) was weighed and dissolved in 60 mL tetrahydrofuran. n-BuLi (2.4 M, 6.5 mL, 15.6 mmol) was added at −20° C., and the mixture was stirred for 1 hour. Triisopropylchlorosilane (20 mmol) was slowly added, then the mixture was refluxed for 24 hours, and 150 mL water and hydrochloric acid (1 M, 150 mL) were added. Precipitates were collected, and washed with water, methanol and n-hexane in sequence. A white solid S6 (4.25 mmol, yield 85%) was obtained.

MALDI-TOF MS: $C_{28}H_{46}S_2Si_2$, m/z calculated value: 502.3; measured value: 502.6.

Calculated values from elemental analysis: C, 66.86; H, 9.22; S, 12.75; Si, 11.17; measured value: C, 66.88; H, 9.25; S, 12.72; Si, 11.15.

a syringe, and stirred at 80° C. for 10 hours. At the end of the reaction, the heating was stopped, the reaction system was cooled to room temperature, and volatile solvent in the reaction system was removed by using a rotary evaporator, so as to obtain a crude product. The crude product was purified by silica gel column chromatography using chlorobenzene as eluent to obtain a solid S7 (1.5 mmol, 75%).

MALDI-TOF MS: $C_{40}H_{68}B_2O_4S_2Si_2$, m/z calculated value: 754.4; measured value: 754.2.

Calculated values from elemental analysis: C, 63.64; H, 9.08; B, 2.86; O, 8.48; S, 8.50; Si, 7.44; measured value: C, 63.66; H, 9.10; B, 2.84; O, 8.50; S, 8.48; Si, 7.42.

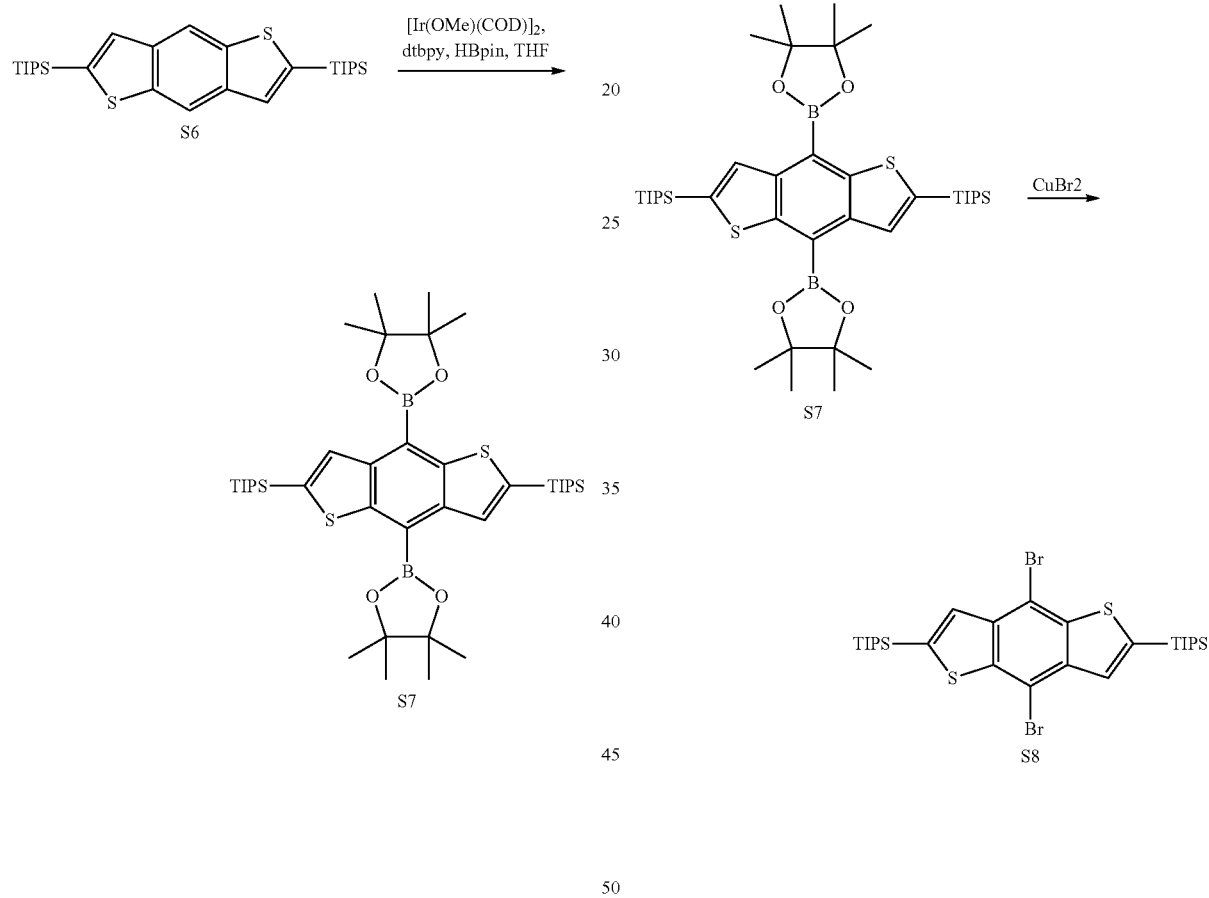

In a nitrogen-filled glove box, a ruthenium catalyst [Ir(OMe)(COD)]₂ (10 μmol) was weighed and added into a one-necked round bottom flask (5 mL). Then HBP in (4 mmol) was weighed and added to the flask and stirred for 2 minutes, and the solution appeared brownish yellow. 4,4'-di-tert-butylbipyridine (dtbpy) (20 μmol) was added to the 5 mL single-necked flask, and stirred for 3 minutes to obtain a wine-red catalyst mixture. Compound S6 (2 mmol) was weighed and added into a two-necked flask (250 mL). The two flasks were sealed in the glove box and then moved out of the glove box. 100 mL dehydrated cyclohexane was added to the two-necked flask (250 mL) to obtain a solution of the Compound S6, which was then stirred at 80° C. for 5 min. The wine-red catalyst mixture in the one-necked flask was injected into the solution of the Compound S6 by using Compound S7 (2 mmol) and CuBr₂ (4 mmol) were weighed and added into a NMP-methanol-water mixed solvent (100 mL, 5:2:1) to form a suspension and then refluxed for 12 hours. The mixture was cooled, and poured into aqueous HCl (1M, 150 mL) to precipitate a crude product. Filtration was carried and a solid crude product was collected. The solid crude product was washed with n-hexane to obtain a solid product S8 (1.5 mmol, 75%)

MALDI-TOF MS: $C_{28}H_{44}Br_2S_2Si_2$, m/z calculated value: 658.1; measured value: 658.4.

Calculated values from elemental analysis: C, 50.90; H, 6.71; Br, 24.19; S, 9.71; Si, 8.50; measured value: C, 50.92; H, 6.73 Br, 24.17 S, 9.70 Si, 8.49.

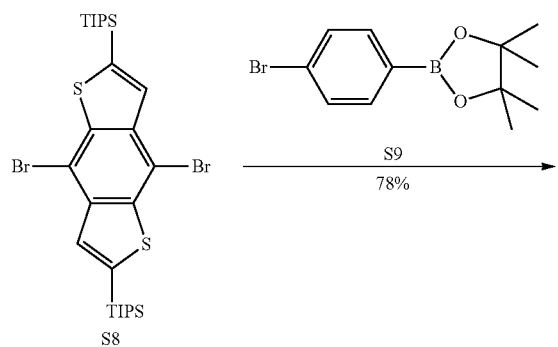

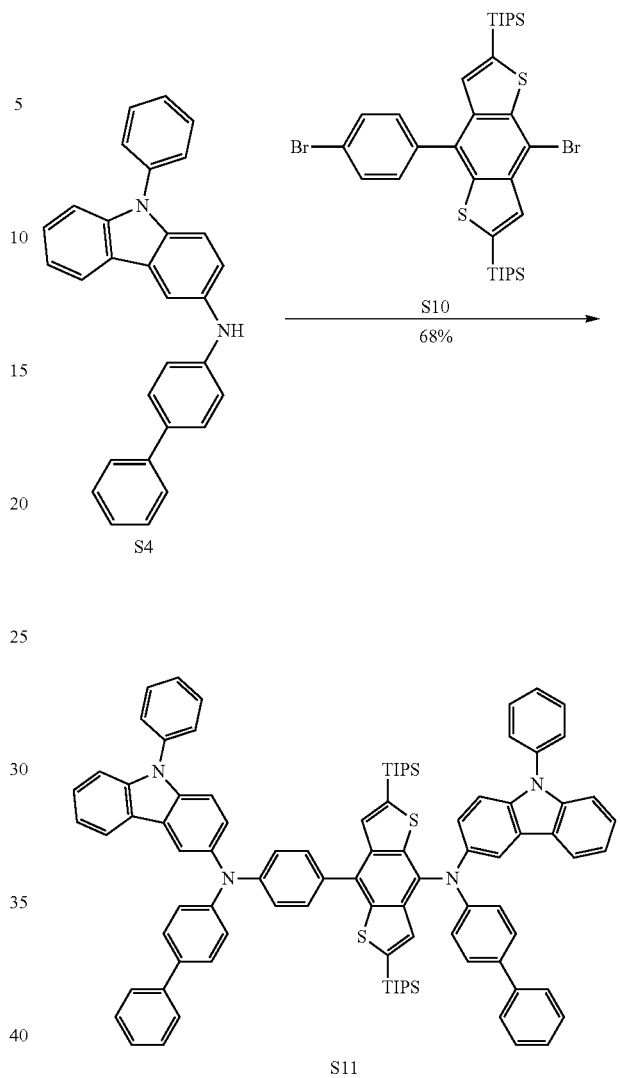

Under protection of nitrogen, Compound S8 (25 mmol), Compound S9 (25 mmol), [Pd$_2$(dba)$_3$].CHCl$_3$ (0.5 mmol), and HP(tBu)$_3$.BF$_4$ (1.0 mmol) were weighed and added to a two-necked flask (250 mL). 100 mL toluene (deoxygenated with N$_2$ for 15 minutes in advance) was injected into the two-necked flask, then 1M K$_2$CO$_3$ water solution (12 mL, deoxygenated with N$_2$ for 15 minutes in advance) was added dropwise, and the mixture was stirred overnight at room temperature. After the reaction was completed, 100 mL deionized water and then a few drops of 2 M HCl were added. The mixture was extracted with dichloromethane, and the organic phase was collected and dried with anhydrous Na$_2$SO$_4$. The filtered and dried organic phase was distillated by a rotary evaporator to remove solvent, so as to obtain a crude product. The crude product was purified by silica gel chromatography column to obtain a solid S10 (19.5 mmol, 78%).

MALDI-TOF MS: C$_{34}$H$_{48}$Br$_2$S$_2$Si$_2$, m/z calculated value: 734.1; measured value: 734.3.

Calculated values from elemental analysis: C, 55.42; H, 6.57; Br, 21.69; S, 8.70; Si, 7.62; measured value: C, 55.45; H, 6.59; Br, 21.67; S, 8.69; Si, 7.60.

Compound S10 (10 mmol), Compound S4 (21.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was quickly degased for 3 times while stirring, after carrying out nitrogen replacement, 20 mL toluene was added by a syringe. The mixture was refluxed for 3 hours under a nitrogen stream, and then cooled to room temperature. Water was added to the cooled reaction mixture, extraction was performed with dichloromethane, and the organic phase was washed with saturated salt water. After the organic phase was dried with anhydrous sodium sulfate, solvent in the organic phase was removed by distillation to obtain a crude product. The crude product was purified by column chromatography to obtain an intermediate S11 (6.8 mmol, 68%).

MALDI-TOF MS: C$_{94}$H$_{90}$N$_4$S$_2$Si$_2$, m/z calculated value: 1394.6; measured value: 1394.8.

Calculated values from elemental analysis: C, 80.87; H, 6.50; N, 4.01; S, 4.59; Si, 4.02; measured value: C, 80.90; H, 6.52; N, 4.00; S, 4.57; Si, 4.00.

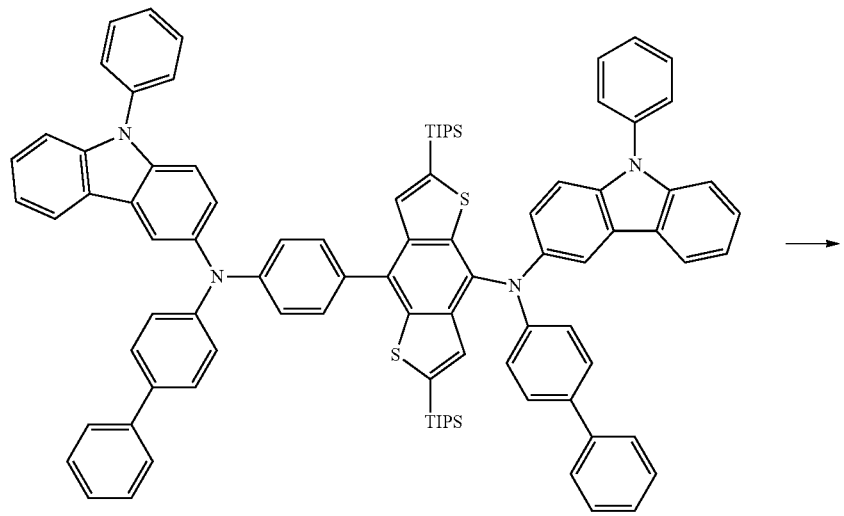
S11
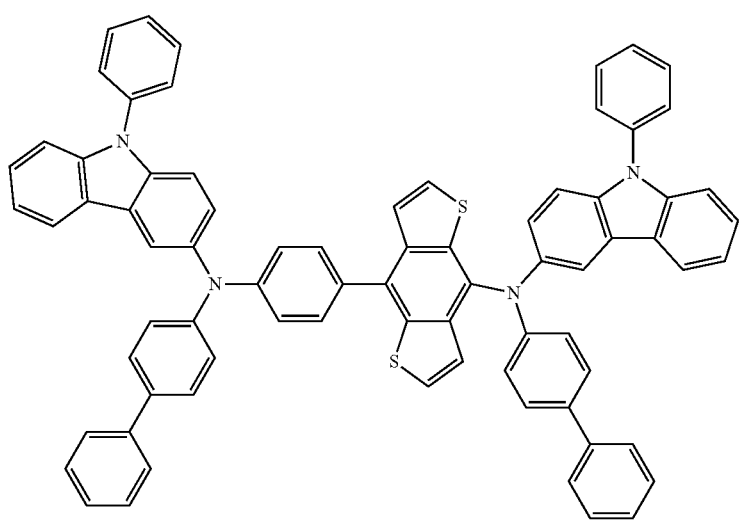
P1

Compound S11 (2 mmol) was weighed and dissolved in tetrahydrofuran (THF) (40 mL). In addition, tetrabutylammonium fluoride (TBAF) (6 mmol) was weighed and dissolved in THF (10 mL). The THF solution of TBAF was added dropwise to the THF solution of the Compound S11. The mixed solution was stirred at room temperature for 30 minutes. Then the solution was concentrated to 8 mL, and the concentrated solution was added dropwise to 30 mL of cold methanol to precipitate a crude product. By using THF as eluent, the crude product was purified by size exclusion column chromatography (SEC), so as to obtain a solid product P1 (1.64 mmol, 82%).

MALDI-TOF MS: $C_{76}H_{50}N_4S_2$, m/z calculated value: 1082.4; measured value: 1082.5.

Calculated values from elemental analysis: C, 84.26; H, 4.65; N, 5.17; S, 5.92; measured value: C, 84.29; H, 4.67; N, 5.14; S, 5.90.

Example 2

Synthesis of Compound P2:

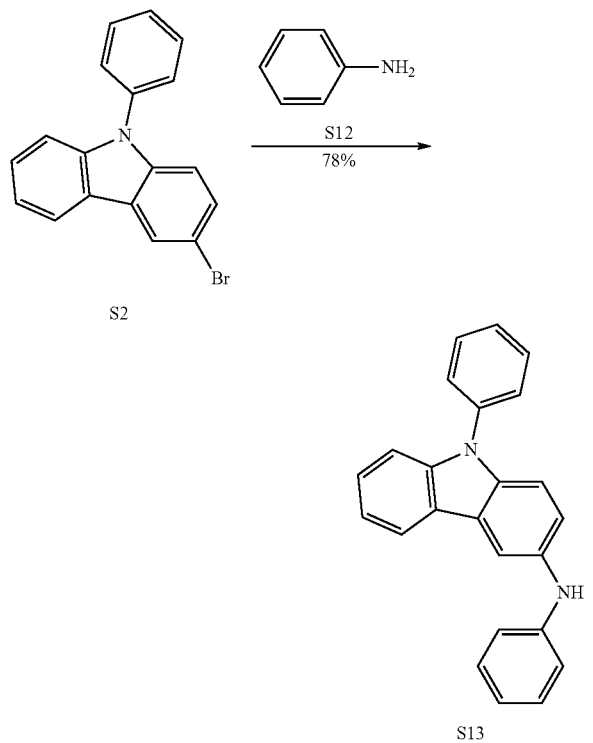

Compound S2 (10 mmol), Compound S12 (10.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was quickly degased for 3 times while stirring, after carrying out nitrogen replacement, 20 mL toluene was added by a syringe. The mixture was refluxed for 3 hours under a nitrogen stream, and then cooled to room temperature. Water was added to the cooled reaction mixture, extraction was performed with dichloromethane, and the organic phase was washed with saturated salt water. After the organic phase was dried with anhydrous sodium sulfate, solvent in the organic phase was removed by distillation and a crude product was obtained. The crude product was purified by column chromatography to obtain Compound S13 (7.8 mmol, 78%).

MALDI-TOF MS: $C_{24}H_{18}N_2$, m/z calculated value: 334.2; measured value: 334.3.

Calculated values from elemental analysis: C, 86.20; H, 5.43; N, 8.38; measured value: C, 86.22; H, 5.41; N, 8.37.

Compound S10 (10 mmol), Compound S13 (21.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was quickly degased for 3 times while stirring, after carrying out nitrogen replacement, 20 mL toluene was added by a syringe. The mixture was refluxed for 3 hours under a nitrogen stream, and then cooled to room temperature. Water was added to the cooled reaction mixture, extraction was performed with dichloromethane, and the organic phase was washed with saturated salt water. After the organic phase was dried with anhydrous sodium sulfate, solvent in the organic phase was removed by distillation and a crude product was obtained. The crude product was purified by column chromatography to obtain an intermediate S14 (7.3 mmol, 73%).

MALDI-TOF MS: $C_{82}H_{82}N_4S_2Si_2$, m/z calculated value: 1242.6; measured value: 1242.7.

Calculated values from elemental analysis: C, 79.18; H, 6.64; N, 4.50; S, 5.16; Si, 4.52; measured value: C, 79.20; H, 6.66; N, 4.49; S, 5.14; Si, 4.51.

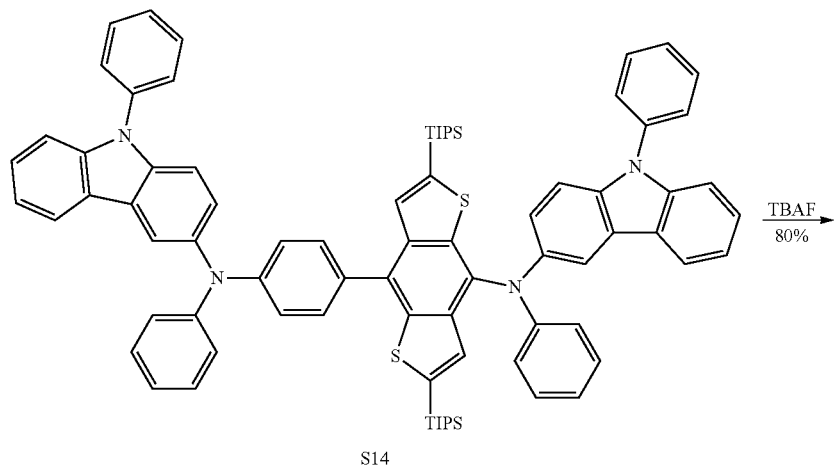

S14

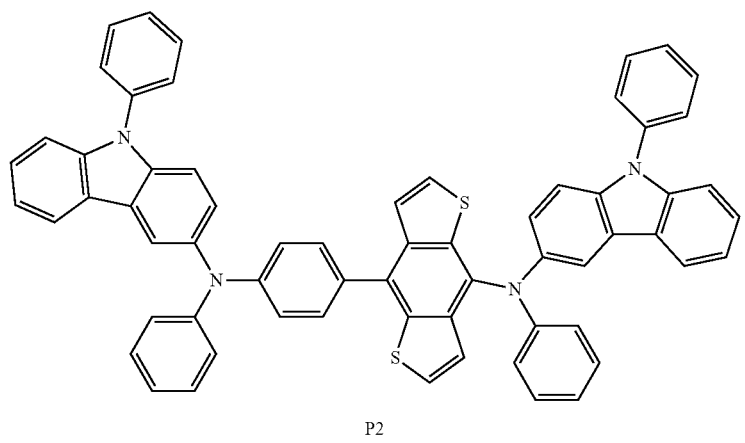

P2

Compound S14 (2 mmol) was weighed and dissolved in THF (40 mL), and TBAF (6 mmol) was weighed and dissolved in THF (10 mL). The THF solution of TBAF was added dropwise to the THF solution of Compound S14. The mixed solution was stirred at room temperature for 30 minutes. Then the solution was concentrated to 8 mL, and the concentrated solution was added dropwise to 30 mL of cold methanol to precipitate a crude product. By using THF as eluent, the crude product was purified by size exclusion column chromatography (SEC), so as to obtain a solid product P2 (1.6 mmol, 80%).

MALDI-TOF MS: $C_{64}H_{42}N_4S_2$, m/z calculated value: 930.3; measured value: 930.5.

Calculated values from elemental analysis: C, 82.55; H, 4.55; N, 6.02; S, 6.89; measured value: C, 82.58; H, 4.57; N, 5.99; S, 6.87.

Example 3

Synthesis of Compound P3:

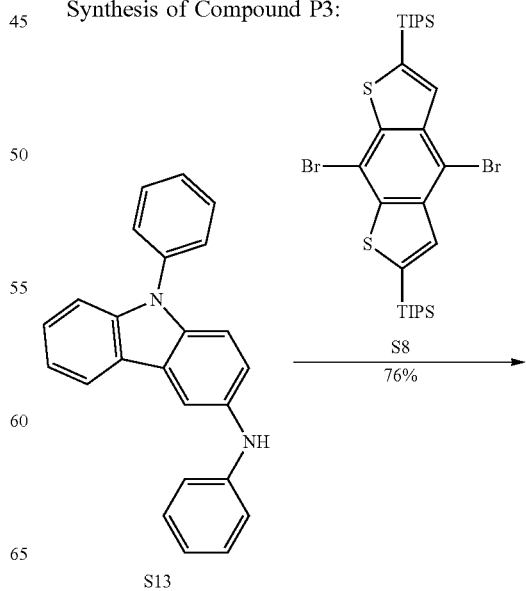

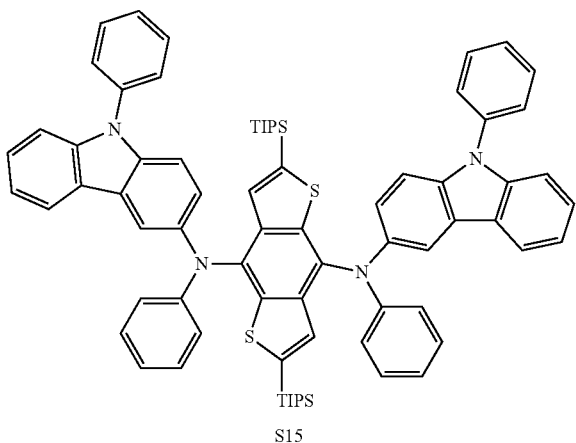

S15

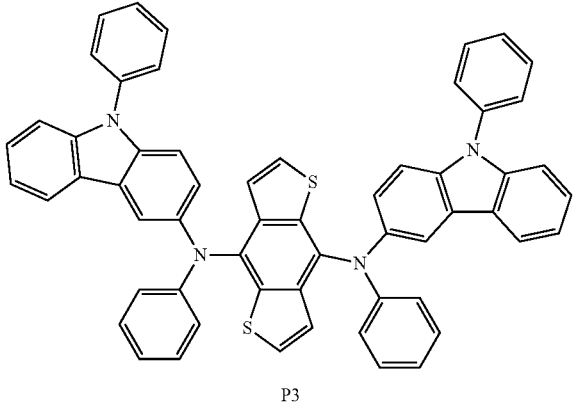

P3

Compound S8 (10 mmol), Compound S13 (21.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was quickly degased for 3 times while stirring, after carrying out nitrogen replacement, 20 mL toluene was added by a syringe. The mixture was refluxed for 3 hours under a nitrogen stream, and then cooled to room temperature. Water was added to the cooled reaction mixture, extraction was performed with dichloromethane, and the organic phase was washed with saturated salt water. After the organic phase is dried with anhydrous sodium sulfate, solvent in the organic phase was removed by distillation and a crude product was obtained. The crude product was purified by column chromatography to obtain an intermediate S15 (7.6 mmol, 76%).

MALDI-TOF MS: $C_{76}H_{78}N_4S_2Si_2$, m/z calculated value: 1166.5; measured value: 1166.6.

Calculated values from elemental analysis: C, 78.17; H, 6.73; N, 4.80; S, 5.49; Si, 4.81; measured value: C, 78.19; H, 6.75; N, 4.79; S, 5.48; Si, 4.79.

Compound S15 (2 mmol) was weighed and dissolved in THF (40 mL), and TBAF (6 mmol) was weighed and dissolved in THF (10 mL). The THF solution of TBAF was added dropwise to the THF solution of S15. The mixed solution was stirred at room temperature for 30 minutes. Then the solution was concentrated to 8 mL, and the concentrated solution was added dropwise to 30 mL of cold methanol to precipitate a crude product. By using THF as eluent, the crude product was purified by size exclusion column chromatography (SEC), so as to obtain a solid product P3 (1.7 mmol, 85%).

MALDI-TOF MS: $C_{58}H_{38}N_4S_2$, m/z calculated value: 854.2; measured value: 854.4.

Calculated values from elemental analysis: C, 81.47; H, 4.48; N, 6.55; S, 7.50; measured value: C, 81.49; H, 4.50; N, 6.53; S, 7.48.

Example 4

Synthesis of Compound P5:

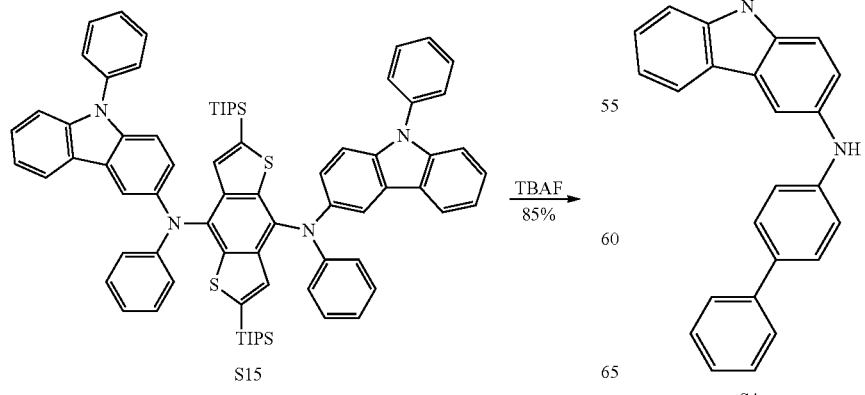

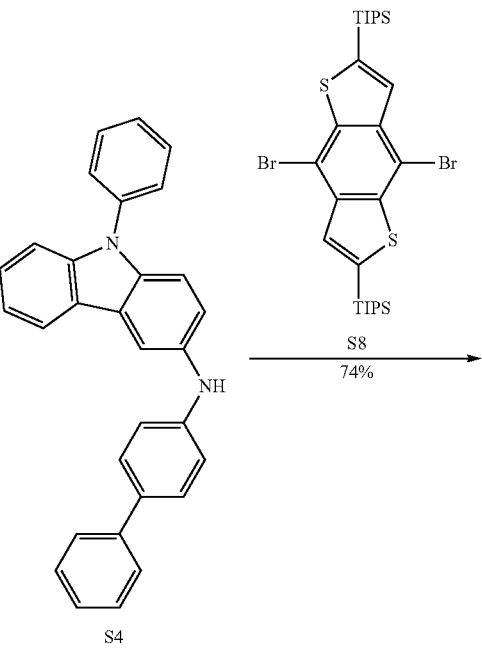

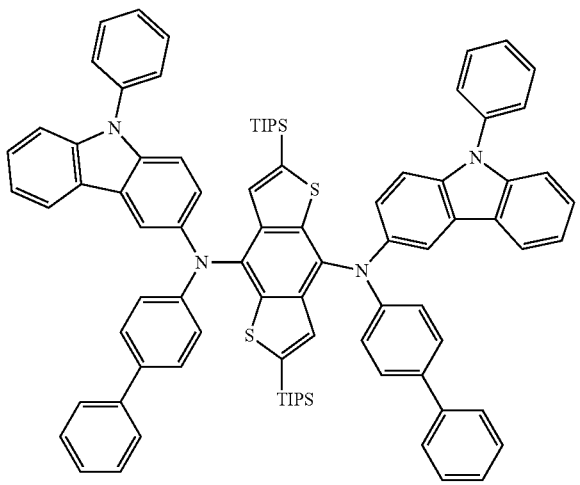

S16

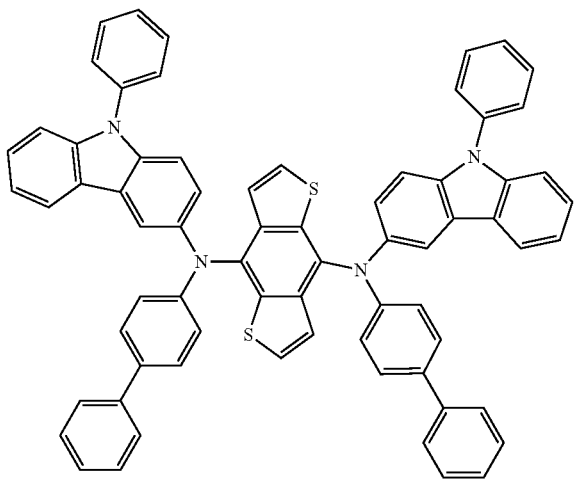

P5

Compound S8 (10 mmol), Compound S4 (21.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was quickly degased for 3 times while stirring, after carrying out nitrogen replacement, 20 mL toluene was added by a syringe. The mixture was refluxed for 3 hours under a nitrogen stream, and then cooled to room temperature. Water was added to the cooled reaction mixture, extraction was performed with dichloromethane, and the organic phase was washed with saturated salt water. After the organic phase is dried with anhydrous sodium sulfate, solvent in the organic phase was removed by distillation and a crude product was obtained. The crude product was purified by column chromatography to obtain an intermediate S16 (7.4 mmol, 74%).

MALDI-TOF MS: $C_{88}H_{86}N_4S_2Si_2$, m/z calculated value: 1318.6; measured value: 1318.8.

Calculated values from elemental analysis: C, 80.07; H, 6.57; N, 4.24; S, 4.86; Si, 4.26; measured value: C, 80.10; H, 6.59; N, 4.23; S, 4.84; Si, 4.24.

Compound S16 (2 mmol) was weighed and dissolved in THF (40 mL), and TBAF (6 mmol) was weighed and dissolved in THF (10 mL). The THF solution of TBAF was added dropwise to the THF solution of S16. The mixed solution was stirred at room temperature for 30 minutes. Then the solution was concentrated to 8 mL, and the concentrated solution was added dropwise to 30 mL of cold methanol to precipitate a crude product. By using tetrahydrofuran as eluent, the crude product was purified by size exclusion column chromatography (SEC), so as to obtain a solid product P5 (1.64 mmol, 82%).

MALDI-TOF MS: $C_{70}H_{46}N_4S_2$, m/z calculated value: 1006.3; measured value: 1006.5.

Calculated values from elemental analysis: C, 83.47; H, 4.60; N, 5.56; S, 6.37; measured value: C, 83.50; H, 4.62; N, 5.53; S, 6.35.

Example 5

Synthesis of Compound P6:

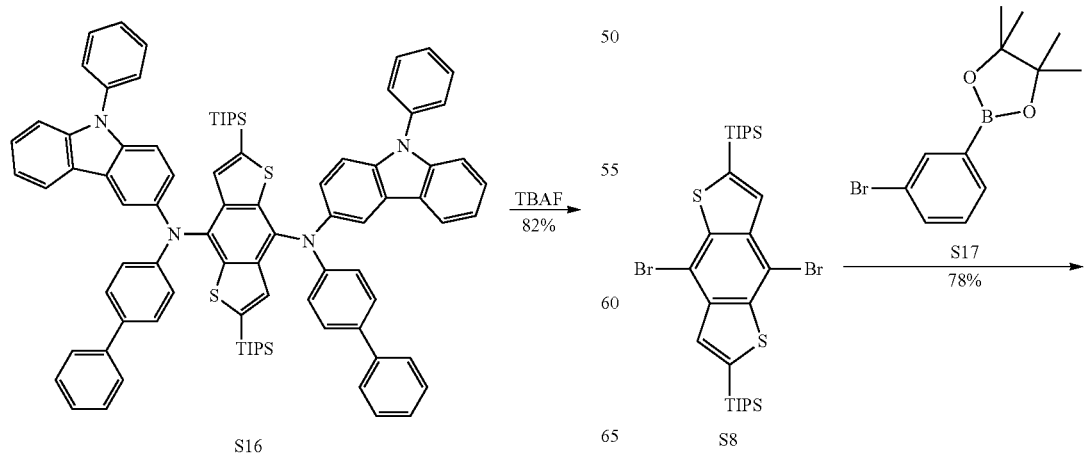

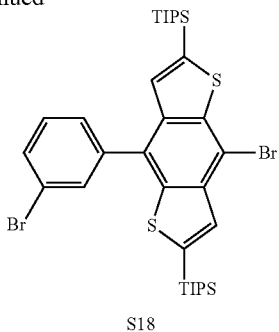

S18

Under protection of nitrogen, Compound S8 (25 mmol), Compound S17 (25 mmol), [Pd$_2$(dba)$_3$].CHCl$_3$ (0.5 mmol), and HP(tBu)$_3$.BF$_4$ (1.0 mmol) were weighed and added to a two-necked flask (250 mL). 100 mL toluene (deoxygenated with N$_2$ for 15 minutes in advance) was injected into the two-necked flask, then 1M K$_2$CO$_3$ water solution (12 mL, deoxygenated with N$_2$ for 15 minutes in advance) was added dropwise, and the mixture was stirred overnight at room temperature. After the reaction was completed, 100 mL deionized water and then a few drops of 2 M HCl were added. Extraction was performed with dichloromethane, and the organic phase was collected and dried with anhydrous Na$_2$SO$_4$. The filtered and dried organic phase was distilled by using a rotary evaporator to remove solvent, and thus a crude product was obtained. The crude product was purified by silica gel chromatography column to obtain a solid S18 (19.5 mmol, 78%).

MALDI-TOF MS: C$_{34}$H$_{48}$Br$_2$S$_2$Si$_2$, m/z calculated value: 734.1; measured value: 734.4.

Calculated values from elemental analysis: C, 55.42; H, 6.57; Br, 21.69; S, 8.70; Si, 7.62; measured value: C, 55.45; H, 6.59; Br, 21.67; S, 8.68; Si, 7.61.

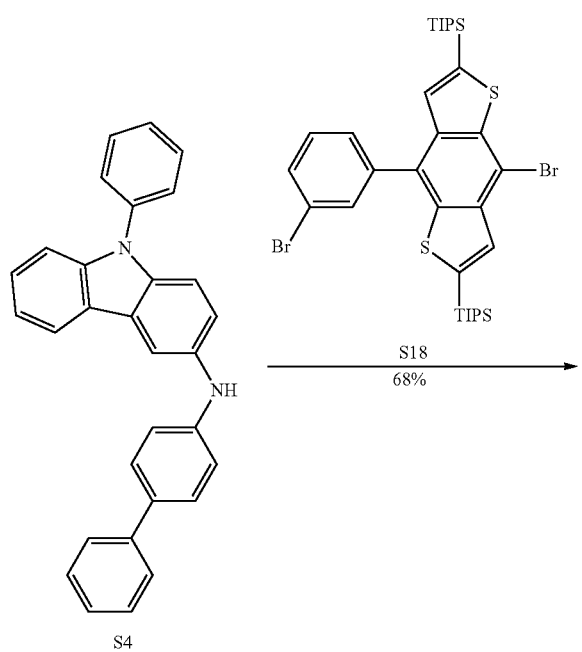

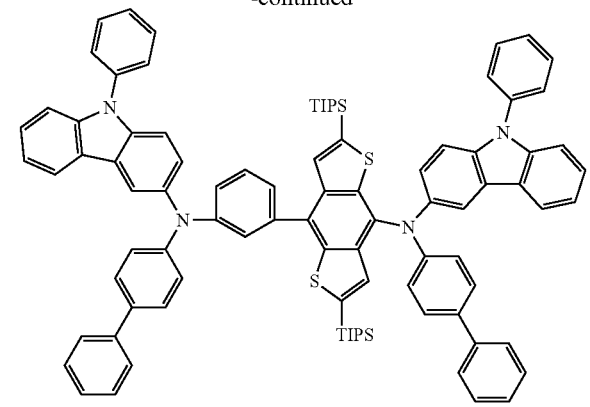

S19

Compound S18 (10 mmol), Compound S4 (21.5 mmol), tris(dibenzylideneacetone) dipalladium (0) (0.05 mmol), sodium tert-butoxide (14 mmol), and tert-butylphosphine (0.2 mmol) were added to a three-necked flask (50 mL). The mixture was quickly degased for 3 times while stirring, after carrying out nitrogen replacement, 20 mL toluene was added by a syringe. The mixture was refluxed for 3 hours under a nitrogen stream, and then cooled to room temperature. Water was added to the cooled reaction mixture, extraction was performed with dichloromethane, and the organic phase was washed with saturated salt water. After the organic phase is dried with anhydrous sodium sulfate, solvent in the organic phase was removed by distillation and a crude product was obtained. The crude product was purified by column chromatography to obtain an intermediate S19 (6.8 mmol, 68%).

MALDI-TOF MS: C$_{94}$H$_{90}$N$_4$S$_2$Si$_2$, m/z calculated value: 1394.6; measured value: 1394.8.

Calculated values from elemental analysis: C, 80.87; H, 6.50; N, 4.01; S, 4.59; Si, 4.02; measured value: C, 80.90; H, 6.52; N, 4.00; S, 4.57; Si, 4.00.

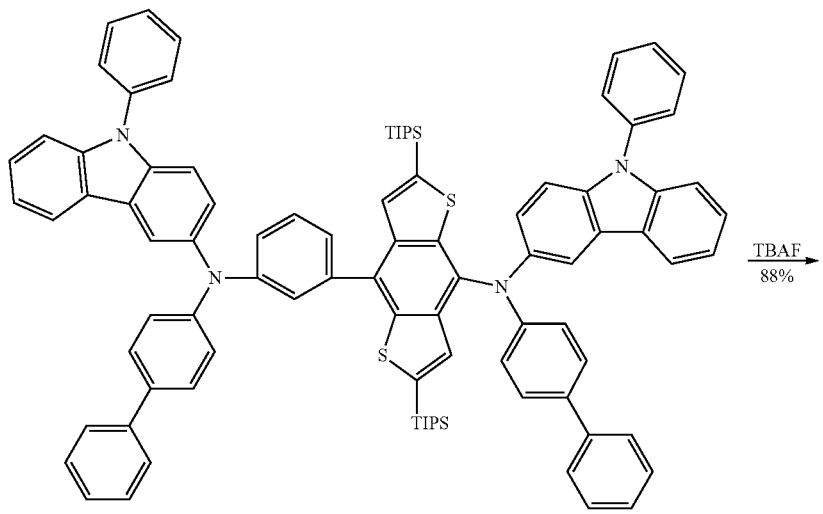

S19

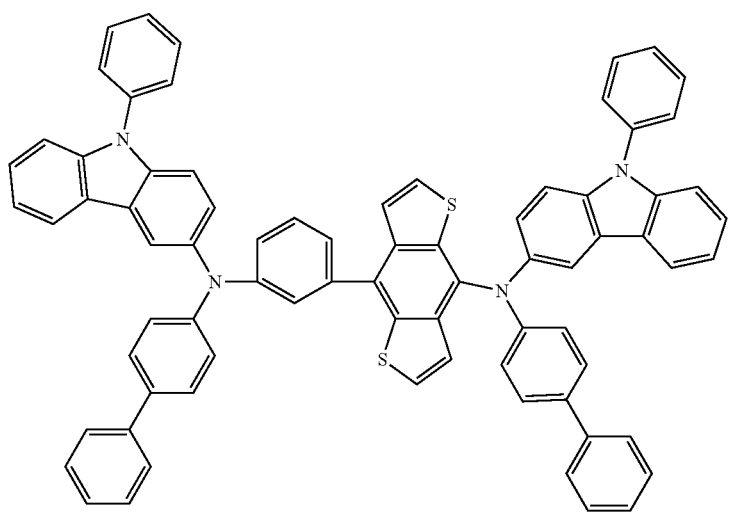

P6

Compound S19 (2 mmol) was weighed and dissolved in THF (40 mL), and TBAF (6 mmol) was weighed and dissolved in THF (10 mL). The THF solution of TBAF was added dropwise to the THF solution of S19. The mixed solution was stirred at room temperature for 30 minutes. Then the solution was concentrated to 8 mL, and the concentrated solution was added dropwise to 30 mL of cold methanol to precipitate a crude product. By using tetrahydrofuran as eluent, the crude product was purified by size exclusion column chromatography (SEC), so as to obtain a solid product P6 (1.76 mmol, 82%).

MALDI-TOF MS: $C_{76}H_{50}N_4S_2$, m/z calculated value: 1082.4; measured value: 1082.6.

Calculated values from elemental analysis: C, 84.26; H, 4.65; N, 5.17; S, 5.92; measured value: C, 84.29; H, 4.67; N, 5.15; S, 5.89.

Table 1 shows respective refractive index (n) and extinction coefficient (k) of several benzo diheterocyclic compounds according to the present disclosure and Comparative Compounds Alq3 and CPL1 with respect to light having different wavelengths (450 nm, 550 nm, 630 nm). The Comparative Compounds Alq3 and CPL1 have the following chemical structures.

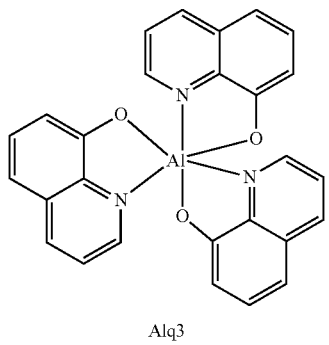

Alq3

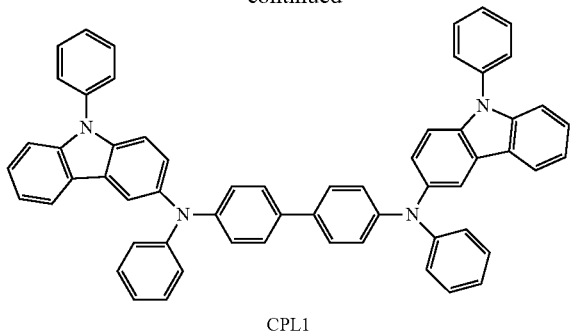

CPL1

TABLE 1

| Compound | $T_g/°C$ | 450 nm | | 550 nm | | 630 nm | |
|---|---|---|---|---|---|---|---|
| | | n | k | n | k | n | k |
| P1 | 162 | 2.34 | 0.092 | 2.09 | 0.000 | 2.03 | 0.000 |
| P2 | 154 | 2.24 | 0.062 | 2.05 | 0.000 | 2.01 | 0.000 |
| P3 | 142 | 2.17 | 0.012 | 1.95 | 0.000 | 1.91 | 0.000 |
| P4 | 148 | 2.26 | 0.048 | 2.03 | 0.000 | 1.98 | 0.000 |
| P5 | 152 | 2.16 | 0.052 | 2.01 | 0.000 | 1.96 | 0.000 |
| P6 | 163 | 2.26 | 0.078 | 2.08 | 0.000 | 2.01 | 0.000 |
| P7 | 160 | 2.22 | 0.072 | 2.06 | 0.000 | 1.97 | 0.000 |
| P8 | 156 | 2.26 | 0.082 | 2.08 | 0.000 | 2.00 | 0.000 |
| P9 | 158 | 2.30 | 0.076 | 2.10 | 0.000 | 2.02 | 0.000 |
| P10 | 164 | 3.34 | 0.092 | 2.10 | 0.000 | 2.03 | 0.000 |
| Alq3 | 149 | 1.78 | 0.156 | 1.73 | 0.000 | 1.71 | 0.000 |
| CPL1 | 150 | 1.96 | 0.001 | 1.83 | 0.000 | 1.78 | 0.000 |

It can be seen from Table 1 that the benzo diheterocyclic compounds according to the present disclosure have higher refractive indexes than the Comparative Compounds Alq3 and CPL1, and thus are more conducive to improving the light extraction efficiency. Meanwhile, in view of extinction coefficient, the benzo diheterocyclic compounds according to the present disclosure have less absorption in blue light region, and thus are suitable to be used as a light extraction material.

The benzo diheterocyclic compounds according to the present disclosure can be used as a material of the capping layer (CPL) of the organic light-emitting component, as well as a material of the auxiliary hole transmission layer and the light-emitting layer.

Example 6 is an embodiment for illustrating technical effects of the nitro benzo diheterocyclic compound according to the present disclosure achieved in practical applications.

Example 6

Organic Light-Emitting Component

Figure 2:
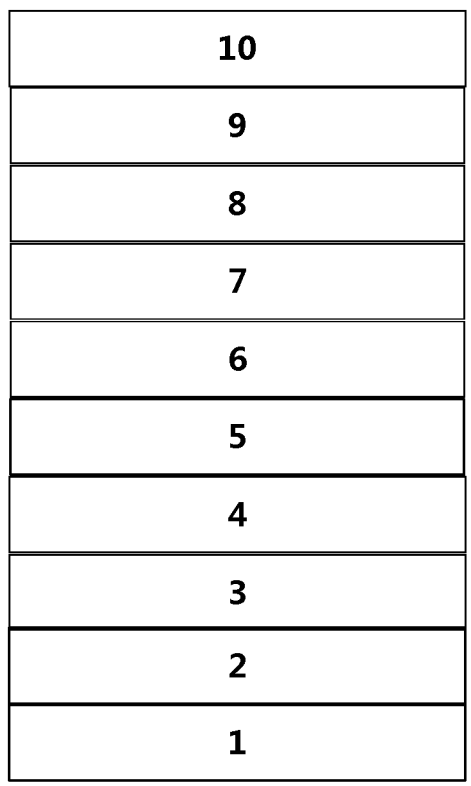
FIG. 2 is a structural schematic diagram of an organic light-emitting component according to an embodiment of the present disclosure.

The OLED component according to the present embodiment has a structure shown in FIG. 2, in which 1 denotes a substrate, 2 denotes an anode, 3 denotes a hole injection layer, 4 denotes a hole transmission layer, 5 denotes an optical auxiliary layer, and 6 denotes a light-emitting layer, 7 denotes an electron transmission layer, 8 denotes an electron injection layer, 9 denotes a cathode, and 10 denotes a capping layer (CPL).

The substrate 1 and the anode 2 of an ITO film having a film thickness of 100 nm was ultrasonically washed with distilled water, acetone, and isopropanol in sequence, dried in an oven, subjected to UV surface treatment for 30 minutes, and then moved to a vacuum vapor deposition chamber. Respective film layers were then vapor-deposited under a vacuum degree of $2\times10^{-6}$ Pa. Compound 1 and Compound 2 (doping weight ratio of 97:3) were vapor-deposited to form the hole injection layer 3 having a thickness of 10 nm, and then Compound 1 was vapor-deposited to form the hole transmission layer (HTL) 4 having a thickness of 100 nm. Compound 3 was vapor-deposited on the hole transmission layer 4 to form the optical auxiliary layer 5 having a thickness of 20 nm. Compound 4, as a doping material of the light-emitting layer 6, and Compound 5, as a host material of the light-emitting layer 6, are vapor-deposited on the optical auxiliary layer 5 at same time, so as to form the light-emitting layer 6 having a thickness of 25 nm. Then Compound 6 and Compound 7 (40:60) were vapor-deposited on the light-emitting layer 6 to form the electron transmission layer (ETL) 7 having a thickness of 50 nm. On the hole transmission layer 7, a LiF layer with a thickness of 2.5 nm and an Ag layer with a thickness of 100 nm were vapor-deposited in sequence, so as to form the electrode injection layer (EIL) 8 and the cathode 9, respectively. Then the capping layer (CPL) 10 having a thickness of 70 nm was formed on a surface on the cathode 9 by vapor deposition. The material of the CPL is selected from a group consisting of the benzo diheterocyclic compounds of the present disclosure. In this way, an organic light-emitting component was obtained.

The organic electroluminescent component can also be prepared by a solution processing method.

The solution processing method includes inkjet printing, spin coating, blade coating, screen printing, roll-to-roll printing, and the like. The solution processing method adopted in the present example was inkjet printing.

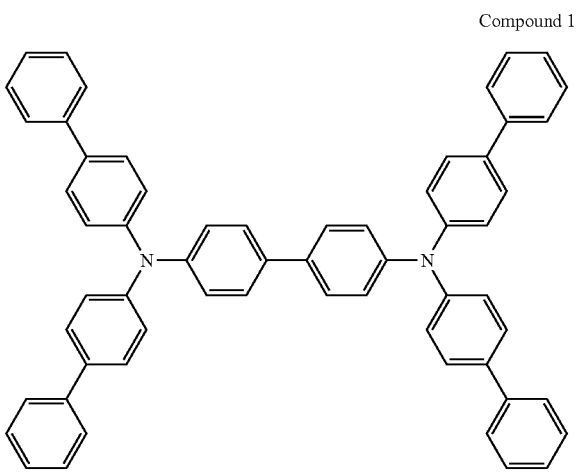

Compound 1

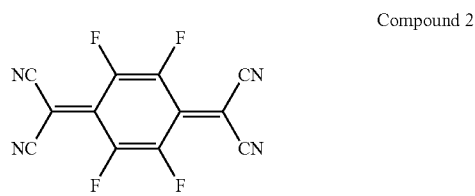

Compound 2

Compound 3

Compound 4

Compound 1

Compound 6

Compound 7

Components 1-10 were prepared in the same manner. In addition, Comparative Components 1-2 were prepared by using Alq3 and CPL1, i.e., the material of CPL in Comparative Component 1 was Alq3, and the material of CPL in Comparative Component 2 was CPL1). In the prepared components merely differ from one another in the material of the CPL, and other layers, such as the light-emitting layer and the auxiliary layer, were the same. These organic light-emitting components were applied with direct current voltage, and their luminescence performances were recorded

TABLE 2

Measurement Results of Luminescence Performances of Components

| No. | Material of CPL | Driving Voltage (V) | Current Efficiency (cd/A)@10 mA/cm$^2$ | Lifespan (Comparing with Comparative Component 2) |
|---|---|---|---|---|
| Component 1 | P1 | 4.14 | 5.42 | 1.16 |
| Component 2 | P2 | 4.12 | 5.28 | 1.10 |
| Component 3 | P3 | 4.09 | 5.24 | 1.16 |
| Component 4 | P4 | 4.08 | 5.36 | 1.10 |
| Component 5 | P5 | 4.14 | 5.38 | 1.09 |
| Component 6 | P6 | 4.15 | 5.26 | 1.14 |
| Component 7 | P7 | 4.10 | 5.35 | 1.18 |
| Component 8 | P8 | 4.12 | 5.28 | 1.15 |
| Component 9 | P9 | 4.13 | 5.36 | 1.12 |
| Component 10 | P10 | 4.12 | 5.40 | 1.15 |
| Comparative Component 1 | Alq3 | 4.15 | 4.86 | 0.95 |
| Comparative Component 2 | CPL1 | 4.10 | 4.92 | 1 |

It can be seen from Table 2 that the Components 1-10 using the benzo diheterocyclic compounds of the present disclosure have a smaller difference in driving voltage, significantly improved current efficiency, and significantly prolonged lifespan as compared with the Comparative Components 1 and 2 using Alq3 and CPL1. This indicates that the light extraction efficiency can be greatly improved by adopting the benzo diheterocyclic compound according to the present disclosure in the capping layer.

In another aspect, the present disclosure provides a display device including the above-mentioned organic light-emitting display panel.

Figure 3:
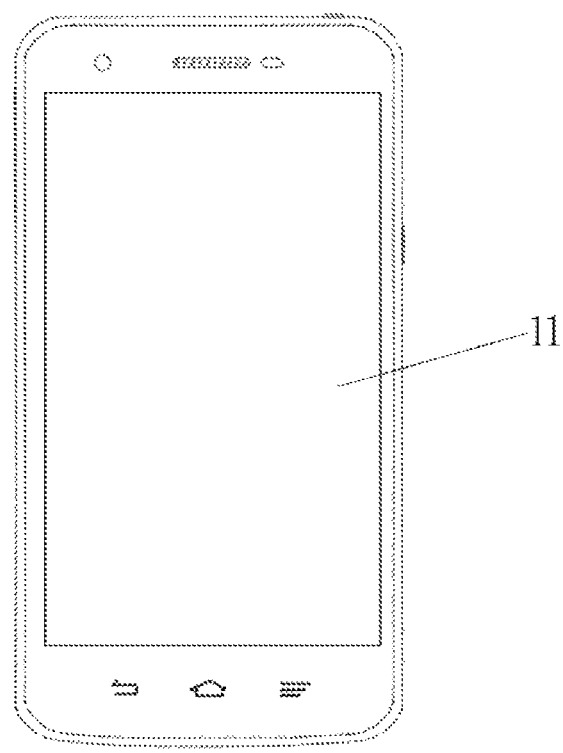
FIG. 3 is a diagram of a display device of the present disclosure.

In the present disclosure, the organic light-emitting component may be an organic light-emitting diode (OLED) that can be used in an organic light-emitting display device. The organic light-emitting display device can be display screen of various smart devices, such a mobile phone display screen, a computer display screen, a liquid crystal television display screen, a smart watch display screen, a display panel of smart car, a display screen of Virtual Reality (VR) or Augmented Reality (AR). FIG. 3 is a schematic diagram of a display device according to an embodiment of the present disclosure, in which 11 denotes a mobile phone display screen.

The preferable embodiments of the present disclosure described above are not intended to limit the scope of the

What is claimed is:

1. A benzo diheterocyclic compound having a structure represented by Formula (I):

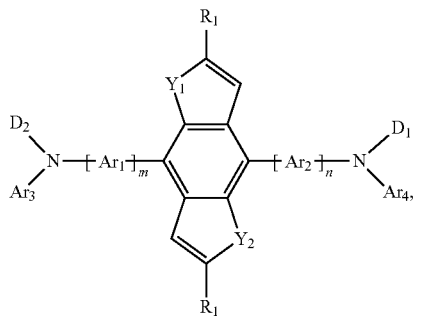

Formula (I)

wherein $Y_1$ and $Y_2$ are each independently selected from oxygen or sulfur;

$R_1$ is selected from a group consisting of hydrogen, phenyl, and naphthyl;

$Ar_1$ and $Ar_2$ are each independently selected from a group consisting of a single bond, substituted or unsubstituted phenyl, a substituted or unsubstituted naphthyl, a substituted or unsubstituted anthracyl, a substituted or unsubstituted phenanthryl, a substituted or unsubstituted acenaphthylenyl, and a substituted or unsubstituted aromatic heterocyclic group;

m and n are integers independently selected from 0 and 1;

$D_1$ and $D_2$ are each independently selected from a group consisting of substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, diarylamino, a diarylamine-derived group, triarylamino and a triarylamine-derived group; and $Ar_3$ and $Ar_4$ are each independently selected from a group consisting of substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, triarylamino and a triarylamine-derived group, wherein when $D_2$ is substituted or unsubstituted phenyl, $Ar_3$ is not a substituted or unsubstituted phenyl, a substituted or unsubstituted biphenyl, or a substituted or unsubstituted naphthyl, and when $D_1$ is substituted or unsubstituted phenyl, $Ar_4$ is not a substituted or unsubstituted phenyl, a substituted or unsubstituted biphenyl, or a substituted or unsubstituted naphthyl.

2. The benzo diheterocyclic compound according to claim 1, having the following chemical structure:

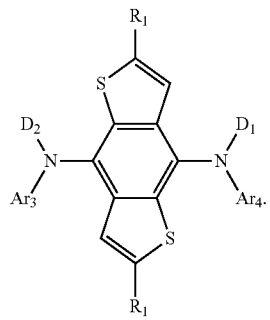

3. The benzo diheterocyclic compound according to claim 1, having the following chemical structure:

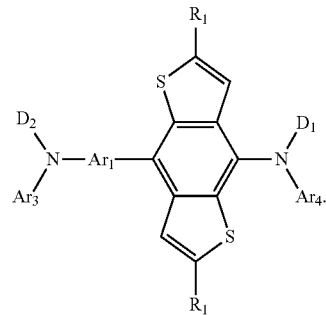

4. The benzo diheterocyclic compound according to claim 1, wherein the substituted or unsubstituted aromatic heterocyclic group is selected from a group consisting of thienyl, thiazolyl, thiadiazolyl, furyl, oxazolyl, and oxadiazolyl.

5. The benzo diheterocyclic compound according to claim 1, wherein $D_1$ and $D_2$ are each independently selected from a group consisting of a carbazole-derived group, an acridine-derived group, diarylamino, a diarylamine-derived group, triarylamino and a triarylamine-derived group, and Ar₃ and Ar₄ are each independently selected from a group consisting of a substituted or unsubstituted phenyl, a substituted or unsubstituted biphenyl, a substituted or unsubstituted naphthyl, and a substituted or unsubstituted anthracyl.

6. The benzo diheterocyclic compound according to claim 1, wherein the carbazole-derived group is selected from a group consisting of the following groups:

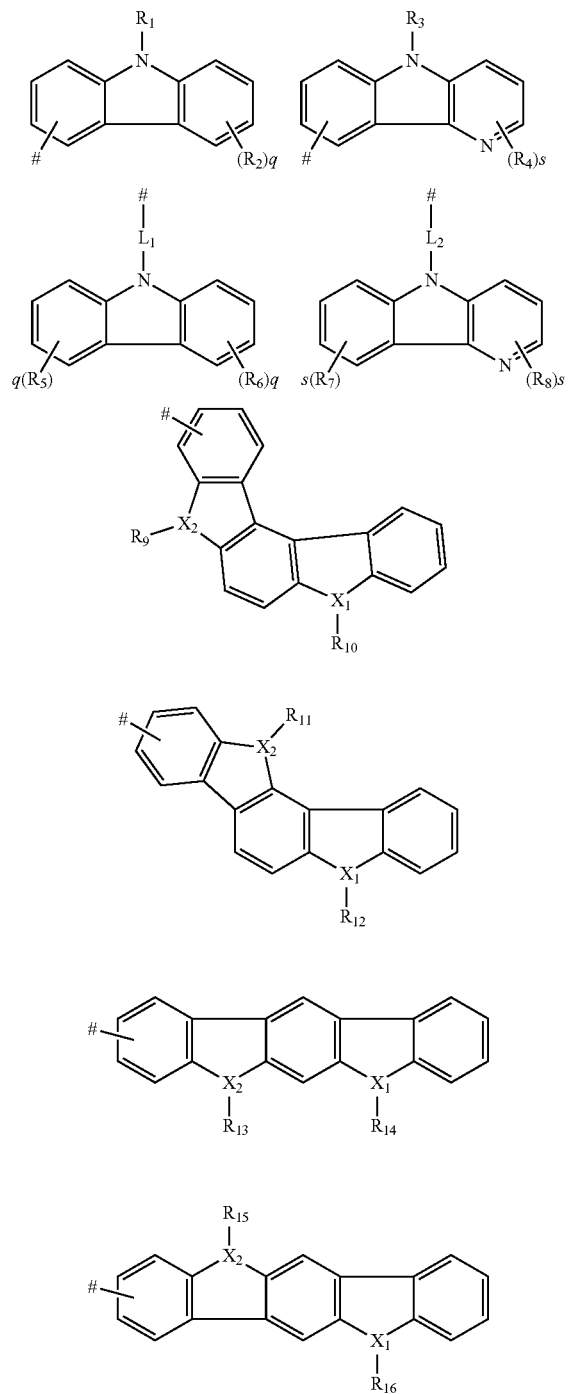

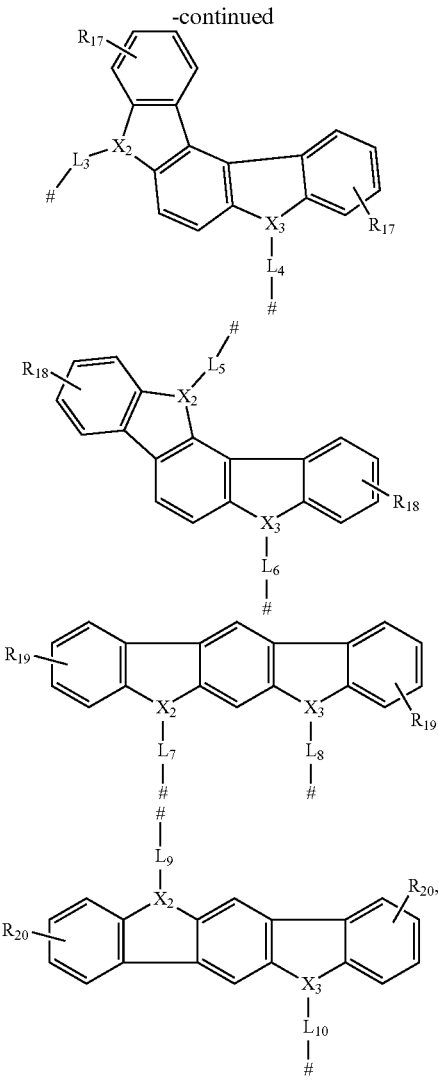

wherein $X_1$, $X_2$ and $X_3$ are each independently selected from a group consisting of carbon, nitrogen, oxygen, sulfur, and silicon, and at least one of $X_1$, $X_2$ and $X_3$ is nitrogen;

$R_1$-$R_{20}$ are each independently selected from a group consisting of alkyl, alkoxy, an aromatic ring group, an aromatic fused ring group, and an aromatic heterocyclic group, and q and s are integers independently selected from 0, 1, 2, and 3;

$L_1$-$L_{10}$ are each independently selected from a group consisting of an aromatic ring group, an aromatic fused ring group, and an aromatic heterocyclic group; and # represents a bonding position.

7. The benzo diheterocyclic compound according to claim 6, wherein the aromatic ring group is phenyl, the aromatic fused ring group is selected from a group consisting of naphthyl, anthracyl, pyrenyl, and perylenyl, and the aromatic heterocyclic group is selected from a group consisting of thienyl, furyl, and thiazolyl.

8. The benzo diheterocyclic compound according to claim 6, wherein the carbazole-derived group is selected from a group consisting of the following groups:

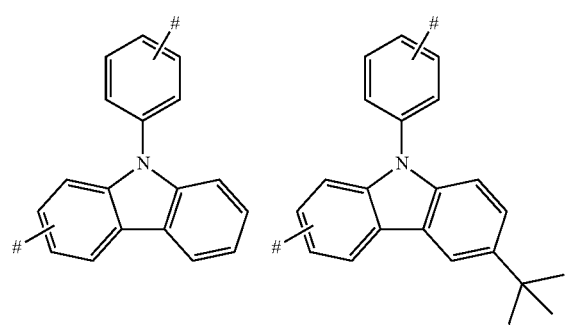
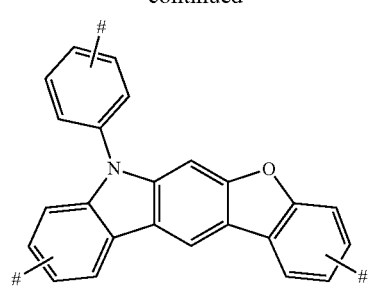
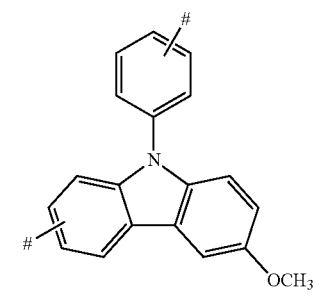
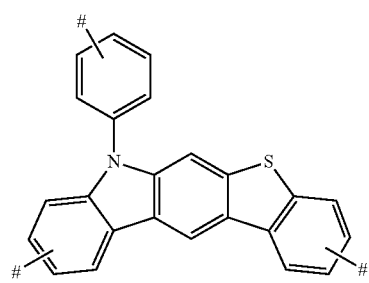
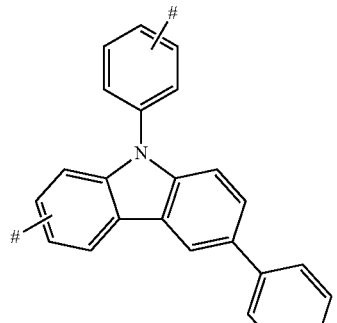
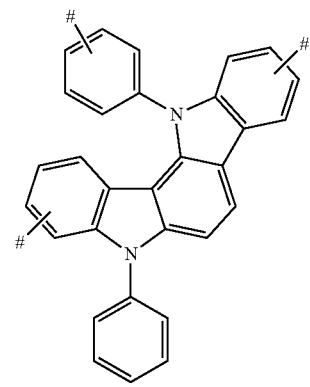
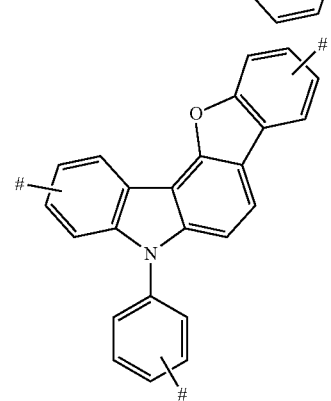
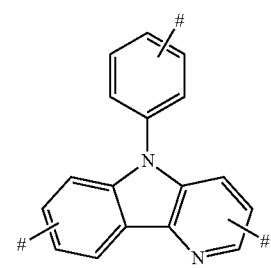
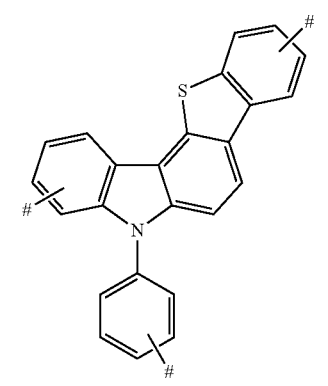
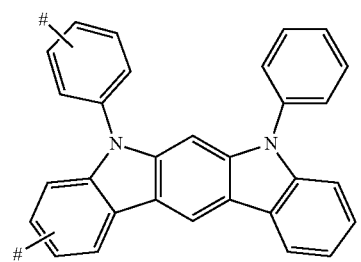

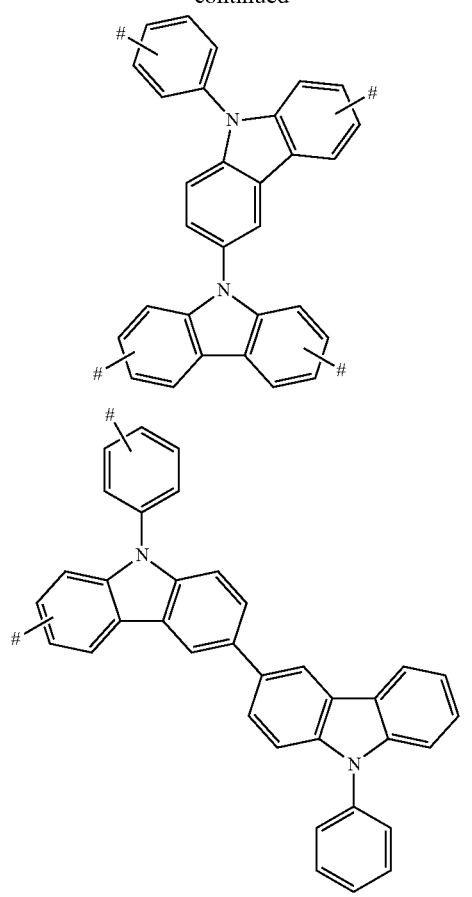
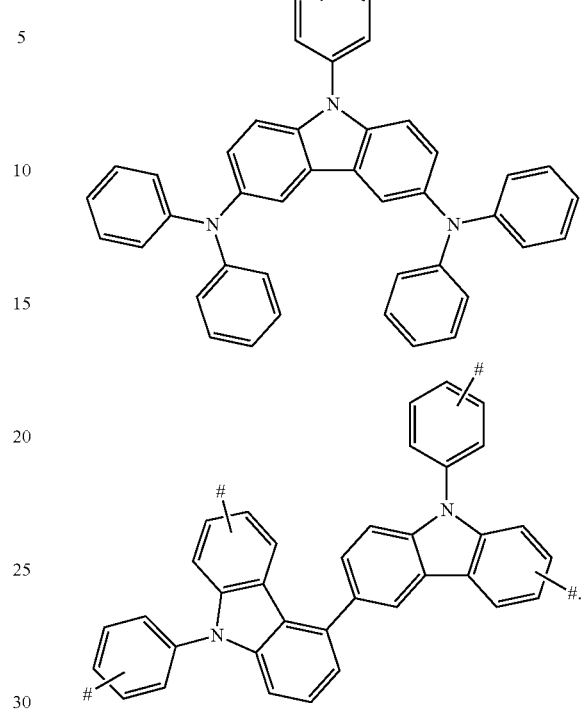
9. The benzo diheterocyclic compound according to claim 1, wherein the acridine-derived group is selected from a group consisting of the following groups:
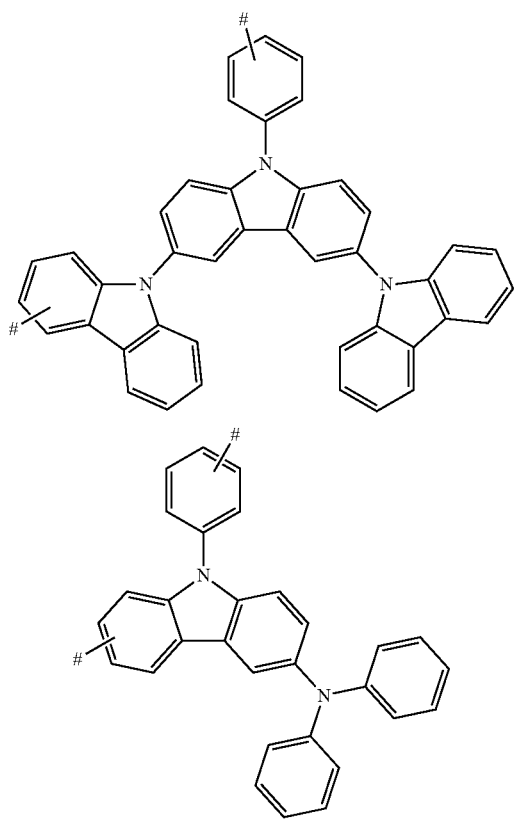
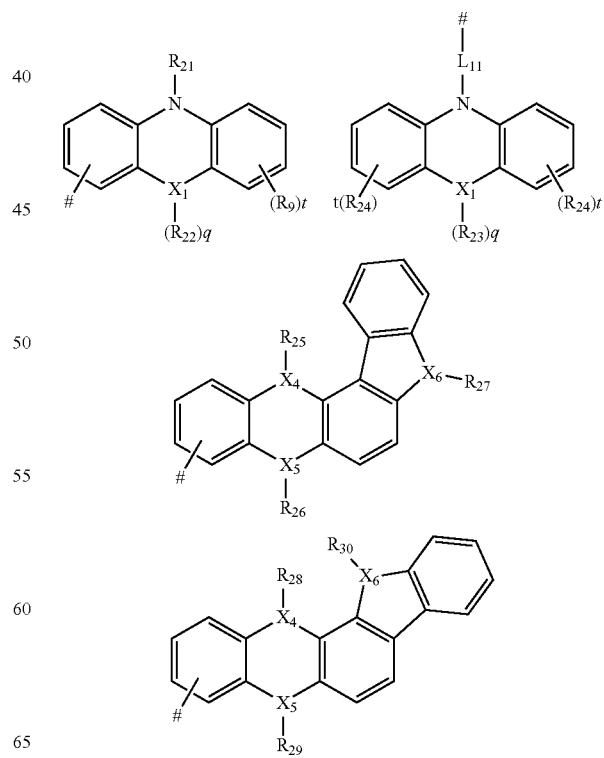

-continued

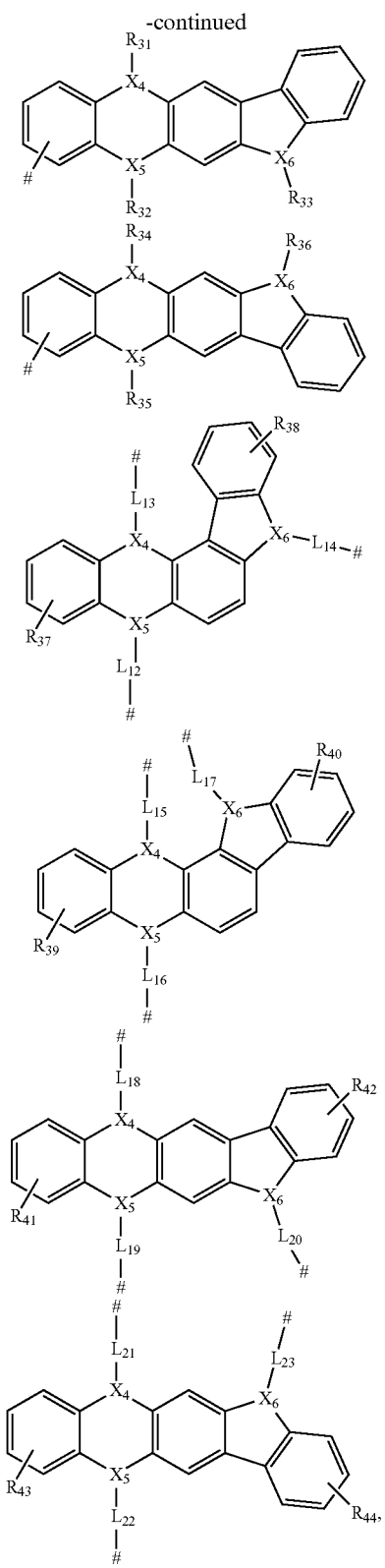

wherein $X_1$, $X_4$, $X_5$, and $X_6$ are each independently selected from a group consisting of carbon, nitrogen, oxygen, sulfur, and silicon, and at least one of $X_4$ and $X_5$ is nitrogen;
$R_{21}$-$R_{44}$ are each independently selected from a group consisting of alkyl, alkoxy, an aromatic ring group, an aromatic fused ring group, and an aromatic heterocyclic group; q and t are integers independently selected from 0, 1, 2, and 3;

$L_{11}$-$L_{23}$ are each independently selected from a group consisting of an aromatic ring group, an aromatic fused ring group, and an aromatic heterocyclic group; and # represents a bonding position.

10. The benzo diheterocyclic compound according to claim 9, wherein the acridine-derived group is selected from a group consisting of the following groups:

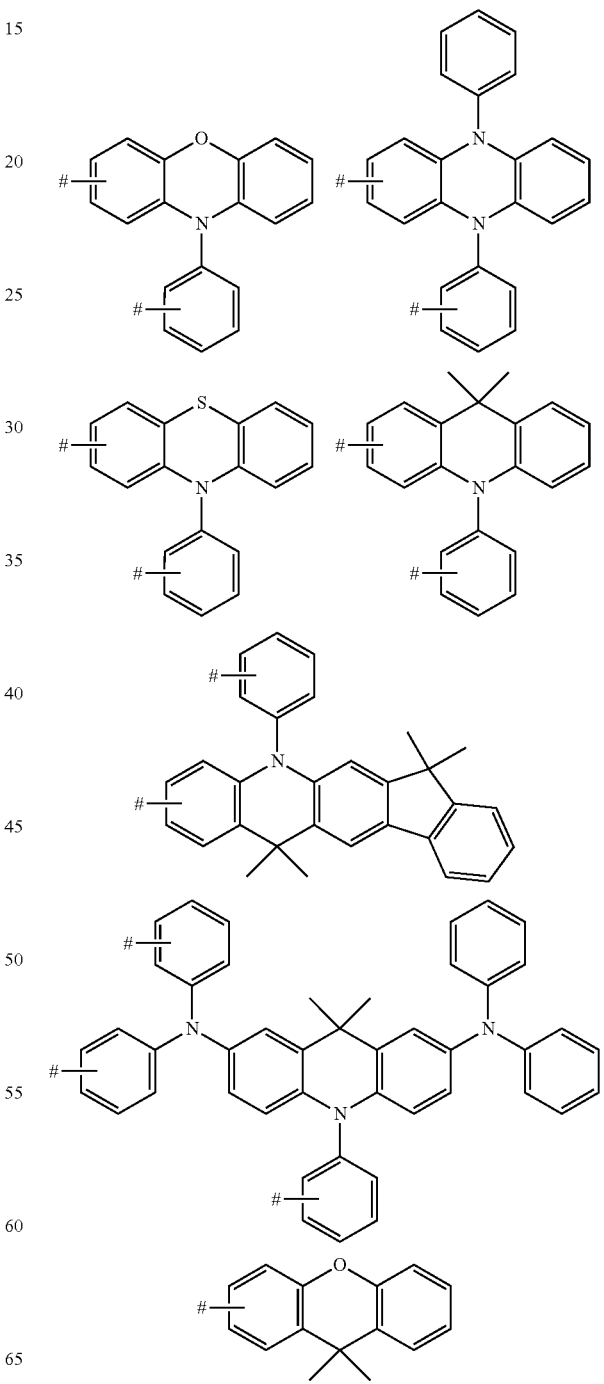

-continued

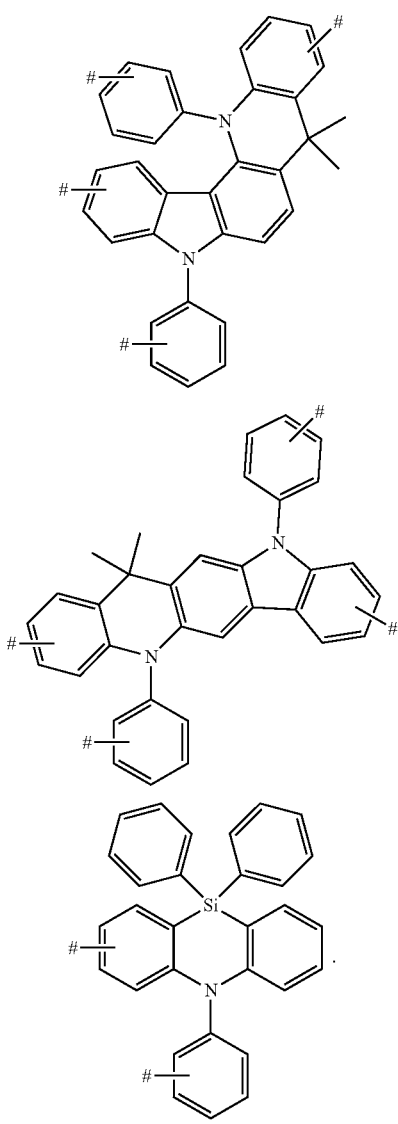

11. The benzo diheterocyclic compound according to claim 1, wherein diarylamino, the diarylamine-derived group, triarylamino or the triarylamine-derived group is selected from a group consisting of the following groups:

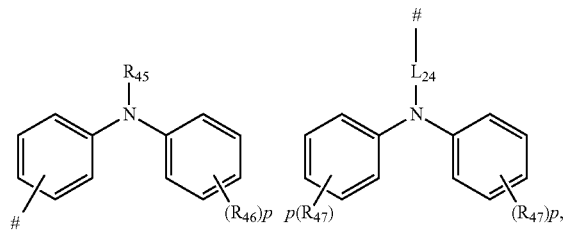

wherein $R_{45}$-$R_{47}$ are each independently selected from a group consisting of alkyl, alkoxy, an aromatic ring group, an aromatic fused ring group, and an aromatic heterocyclic group; p is 0, 1, 2, or 3;

$L_{24}$ is selected from a group consisting of an aromatic ring group, an aromatic fused ring group, and an aromatic heterocyclic group; and # represents a bonding position.

12. The benzo diheterocyclic compound according to claim 11, wherein diarylamino, the diarylamine-derived group, triarylamino or the triarylamine-derived group is selected from a group consisting of the following groups:

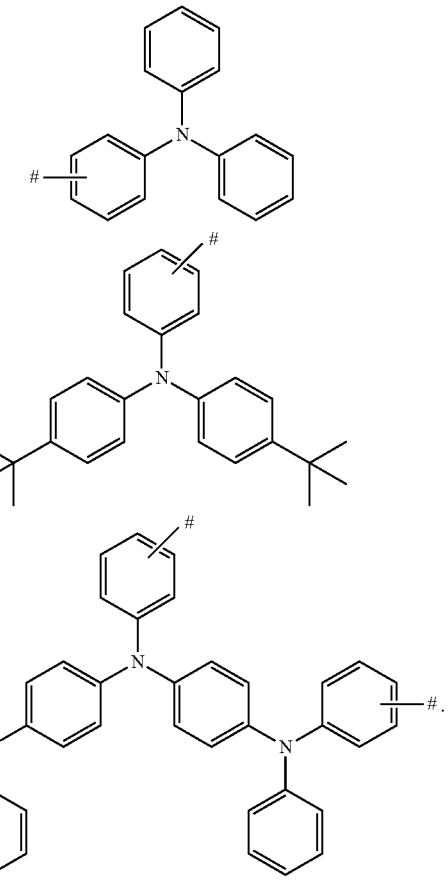

13. The benzo diheterocyclic compound according to claim 1, wherein $D_1$ and $D_2$ are each independently selected from a group consisting of the following groups:

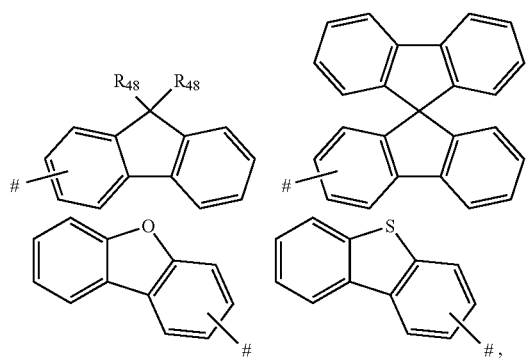

wherein $R_{48}$ is selected from a group consisting of alkyl, alkoxy, an aromatic ring group, an aromatic fused ring group, and an aromatic heterocyclic group.

14. The benzo diheterocyclic compound according to claim 1, being selected from a group consisting of the following groups:
P1
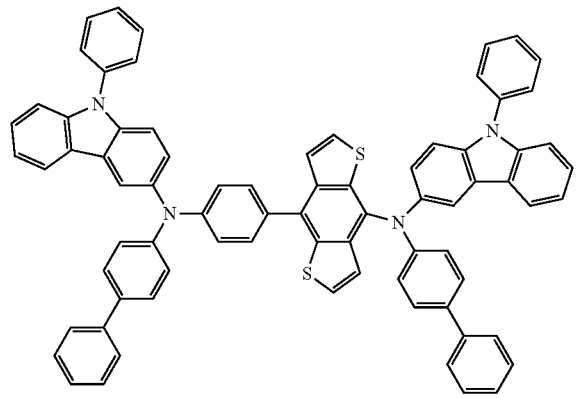
P2
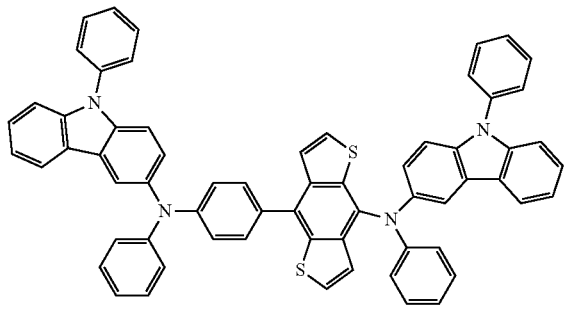
P3
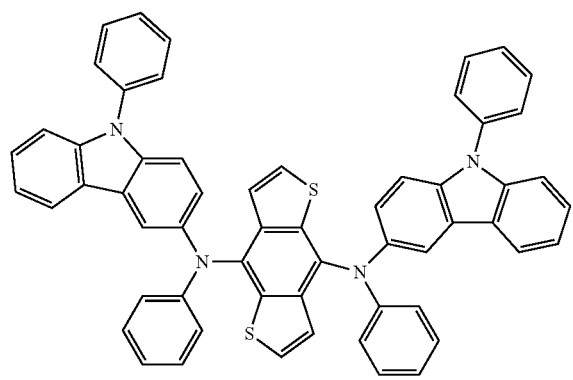
P4
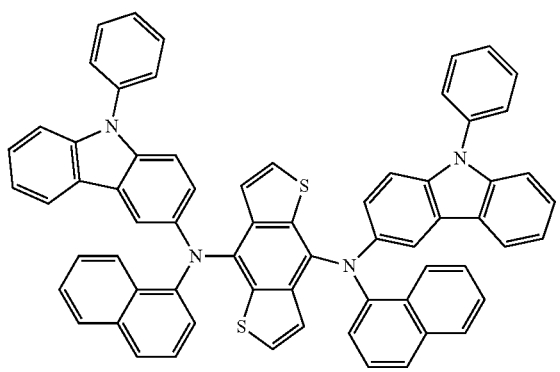
P5
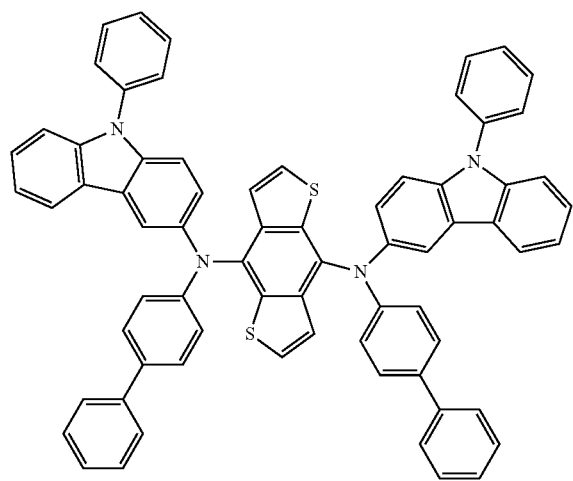
P6
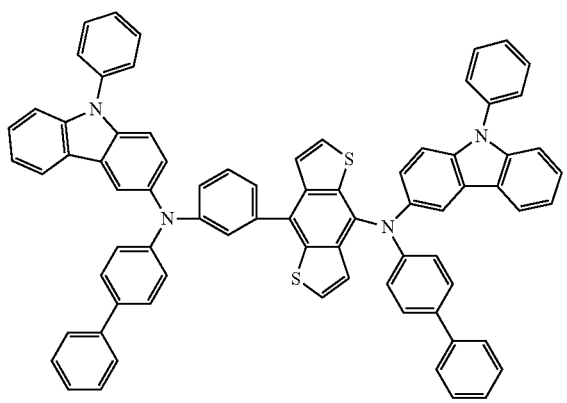

-continued
P7
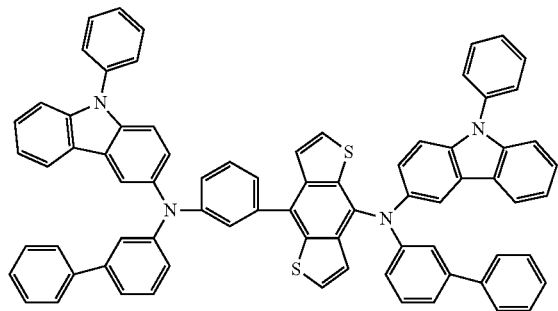
P8
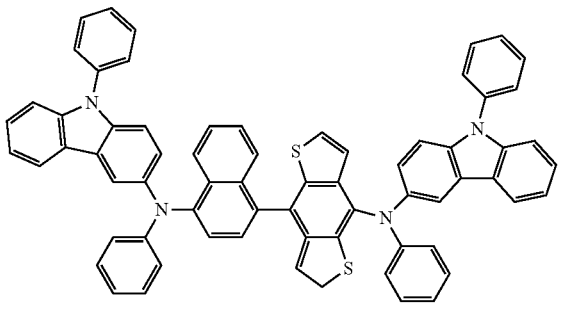
P9
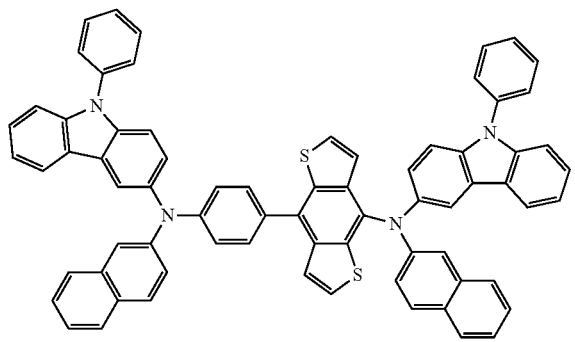
P10
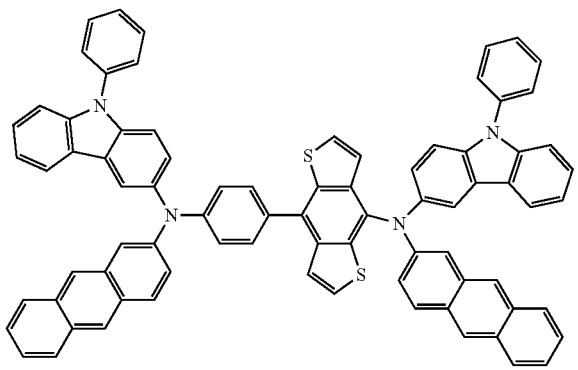
P11
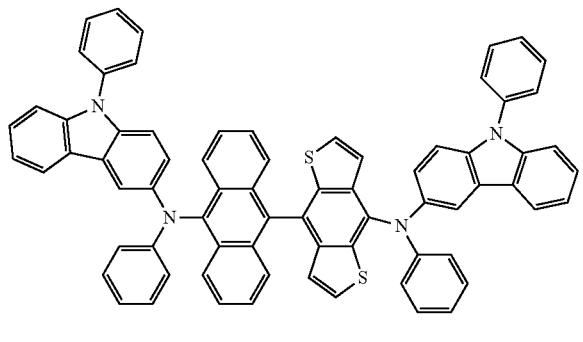
P12
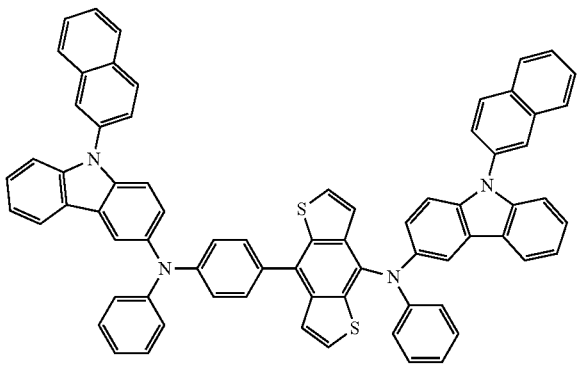
P13
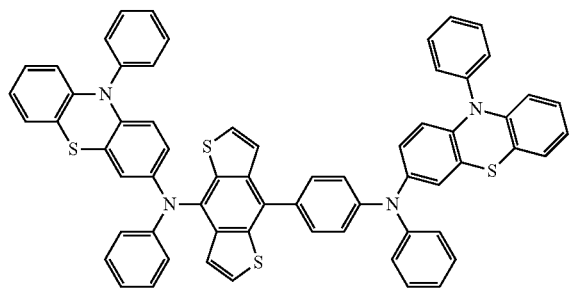
P14
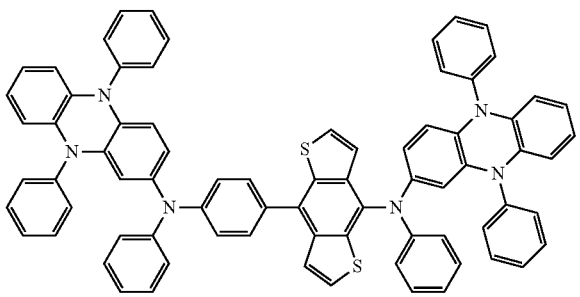

-continued
P15
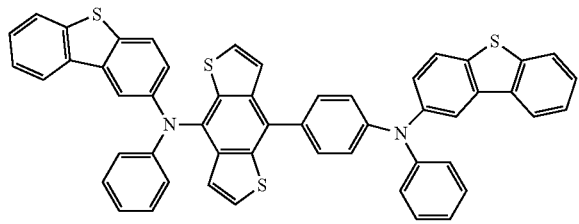
P16
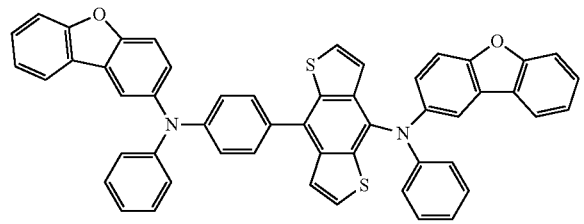
P17
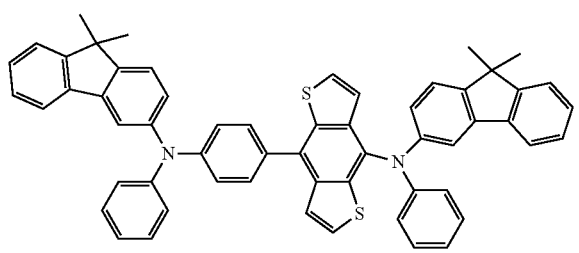
P18
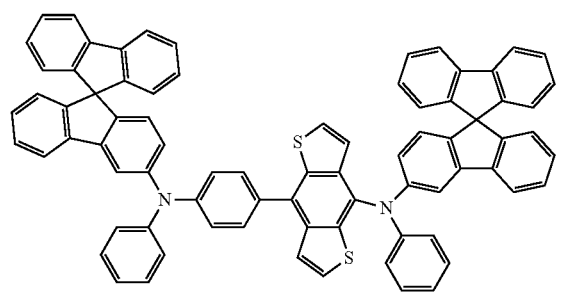
P19
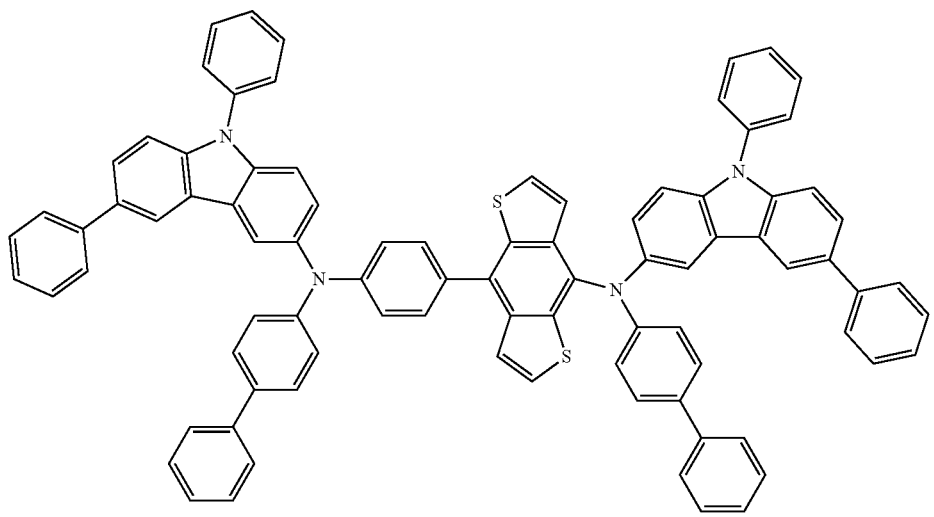
P20
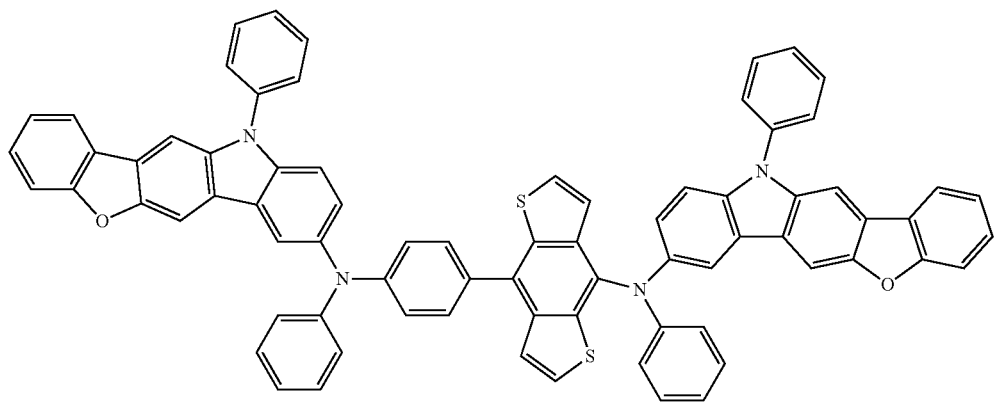

-continued
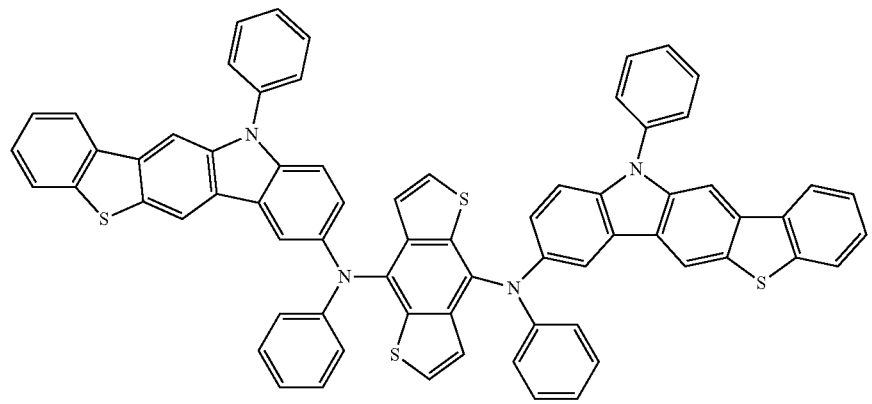
P21
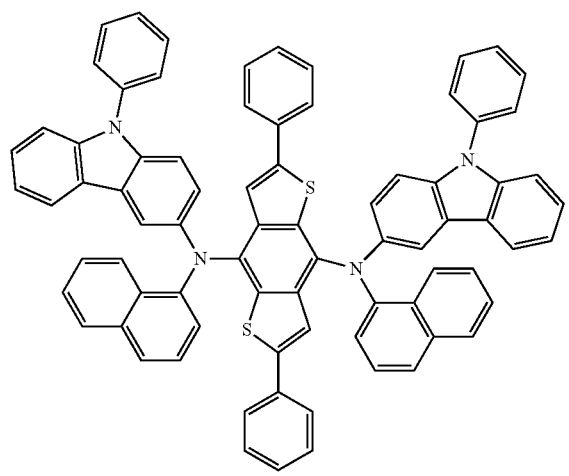
P22
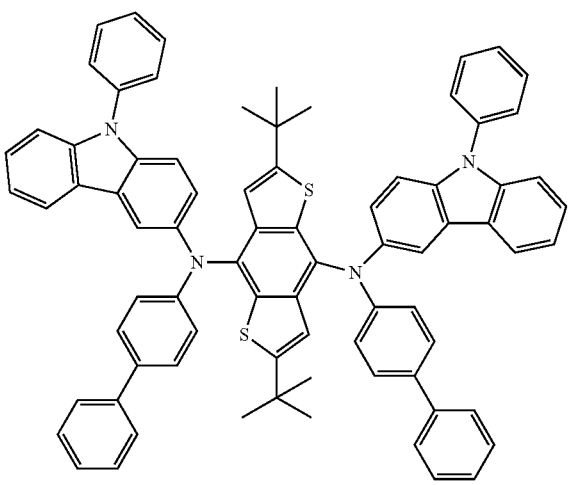
P23
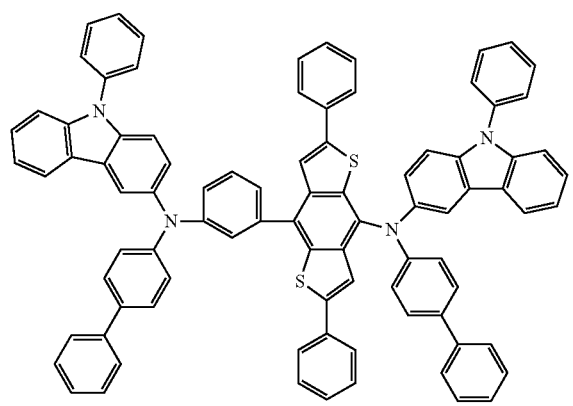
P24
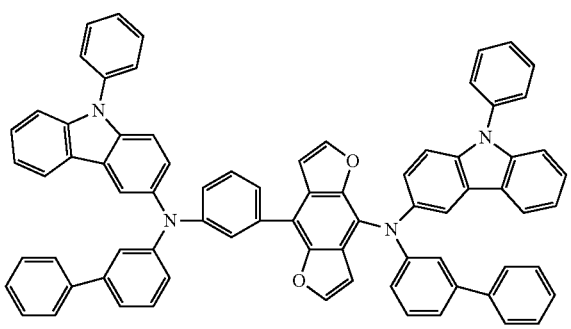
P25

-continued
P26
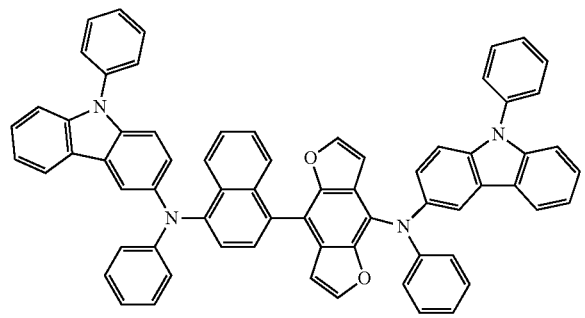
P27
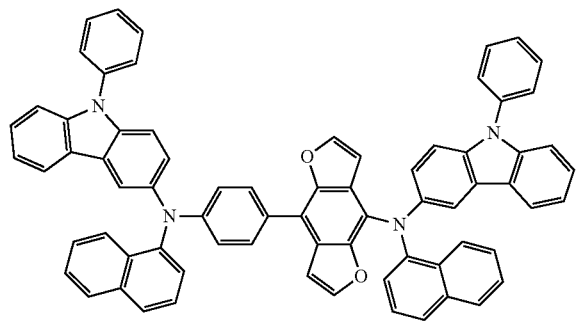
P28
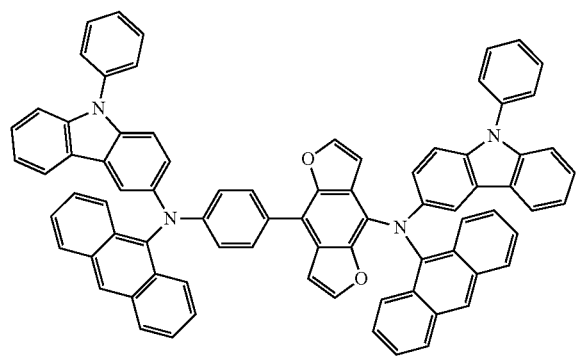
P29
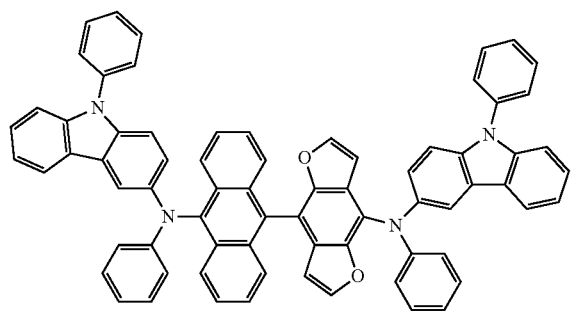
P30
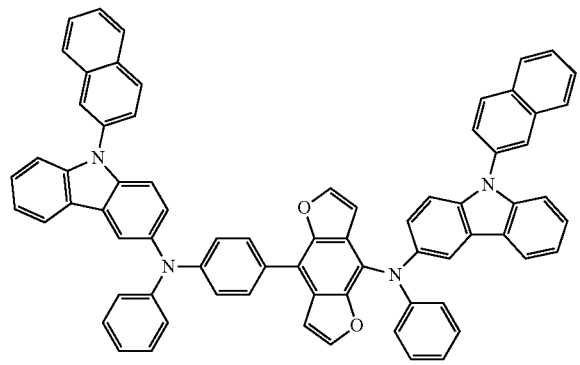
P31
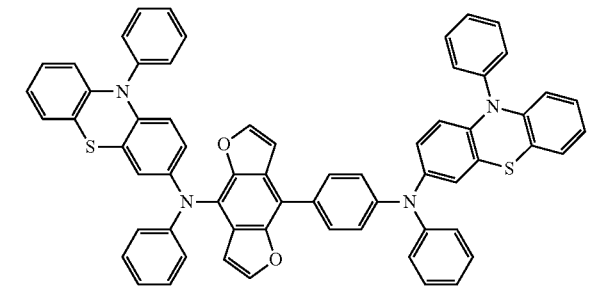
P32
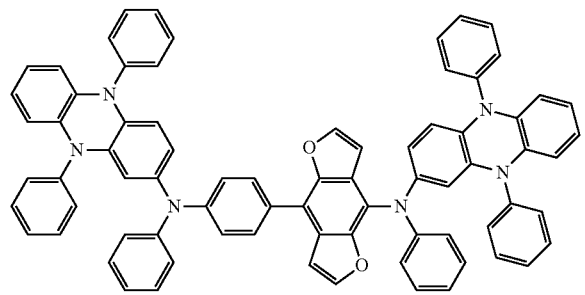
P33
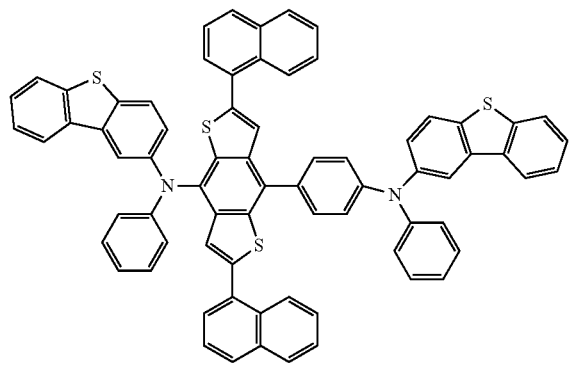

P34

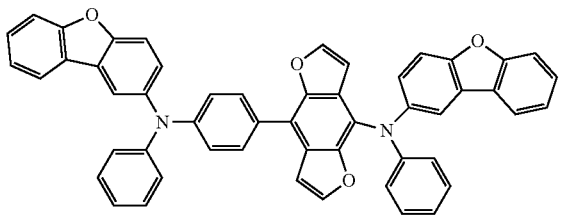

P35

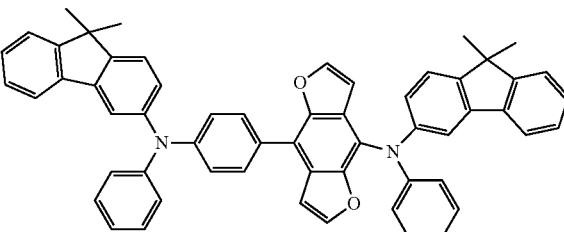

P36

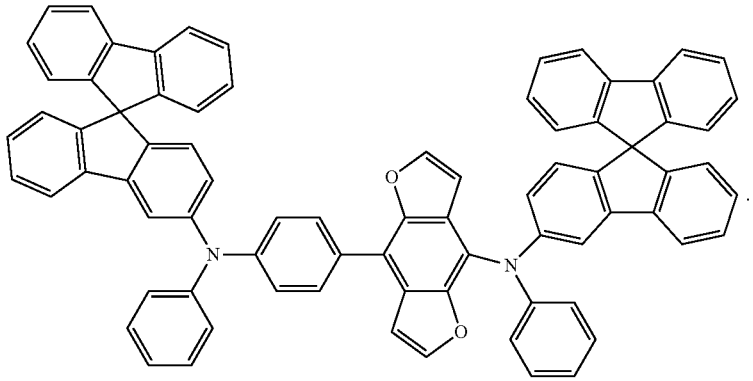

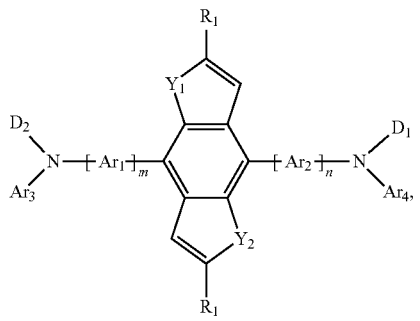

15. The benzo diheterocyclic compound according to claim 14, wherein for a visible light having a wavelength in a range of 450 nm-630 nm, the benzo diheterocyclic compound has a refractive index of 1.85-2.50 and a light extinction coefficient less than 0.1; a difference between refractive indexes of the benzo diheterocyclic compound for a visible light of 450 nm and a visible light of 550 nm is less than 0.35; and a difference between refractive indexes of the benzo diheterocyclic compound for a visible light of 550 nm and a visible light of 630 nm is less than 0.15.

16. A display panel, comprising an organic light-emitting component, wherein the organic light-emitting component comprises an anode, a cathode, a light-emitting layer disposed between the anode and the cathode, and a capping layer covering the cathode, wherein the capping layer comprises one or more benzo diheterocyclic compounds having a structure represented by Formula (I):

Formula (I)

wherein $Y_1$ and $Y_2$ are each independently selected from oxygen or sulfur;
$R_1$ is selected from a group consisting of hydrogen, phenyl, and naphthyl;

$Ar_1$ and $Ar_2$ are each independently selected from a group consisting of a single bond, a substituted or unsubstituted phenyl, a substituted or unsubstituted naphthyl, a substituted or unsubstituted anthracyl, a substituted or unsubstituted phenanthryl, a substituted or unsubstituted acenaphthylenyl, and a substituted or unsubstituted aromatic heterocyclic group; m and n are integers independently selected from 0 and 1;

$D_1$ and $D_2$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, diarylamino, a diarylamine-derived group, triarylamino and a triarylamine-derived group; and $Ar_3$ and $Ar_4$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, triarylamino and a triarylamine-derived group.

17. The display panel according to claim 16, wherein the capping layer has a thickness of 30 nm-100 nm, and
a transmittance of the cathode together with the capping layer for a visible light of 450-630 nm is greater than 65%.

18. The display panel according to claim 16, wherein the organic light-emitting component further comprises one or more of a hole injection layer, a hole transmission layer, an electron blocking layer, a hole blocking layer, an electron transmission layer, and an electron injection layer,
when the organic light-emitting component comprises a hole transmission layer, the hole transmission layer comprises one or more benzo diheterocyclic compounds according to claim 1, and/or
when the organic light-emitting component comprises the light-emitting layer, the light-emitting layer comprises one or more benzo diheterocyclic compounds according to claim 1.

19. The display panel according to claim 16, the organic light-emitting component further comprises an auxiliary hole transmission layer positioned between the light-emitting layer and a hole transmission layer, and
the auxiliary hole transmission layer is configured to control a resonant period of light emitted from the light-emitting layer.

20. A display device, comprising a display panel comprising an organic light-emitting component,
wherein the organic light-emitting component comprises an anode, a cathode, a light-emitting layer disposed between the anode and the cathode, and a capping layer covering the cathode, wherein the capping layer comprises one or more benzo diheterocyclic compounds having a structure represented by Formula (I):

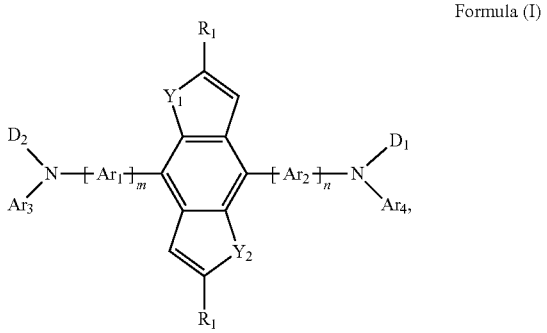

Formula (I)

wherein $Y_1$ and $Y_2$ are each independently selected from oxygen or sulfur;

$R_1$ is selected from a group consisting of hydrogen, phenyl, and naphthyl;

$Ar_1$ and $Ar_2$ are each independently selected from a group consisting of a single bond, a substituted or unsubstituted phenyl, a substituted or unsubstituted naphthyl, a substituted or unsubstituted anthracyl, a substituted or unsubstituted phenanthryl, a substituted or unsubstituted acenaphthylenyl, and a substituted or unsubstituted aromatic heterocyclic group; m and n are integers independently selected from 0 and 1;

$D_1$ and $D_2$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, diarylamino, a diarylamine-derived group, triarylamino and a triarylamine-derived group; and $Ar_3$ and $Ar_4$ are each independently selected from a group consisting of a substituted or unsubstituted phenyl, a substituted or unsubstituted biphenyl, a substituted or unsubstituted naphthyl, a substituted or unsubstituted anthracyl, a substituted or unsubstituted phenanthryl, a substituted or unsubstituted acenaphthylenyl, a substituted or unsubstituted pyrenyl, a substituted or unsubstituted perylenyl, a substituted or unsubstituted fluorenyl, a substituted or unsubstituted spirodifluorenyl, a substituted or unsubstituted chrysenyl, a substituted or unsubstituted benzophenanthryl, a substituted or unsubstituted benzoanthracyl, a substituted or unsubstituted fluoranthenyl, a substituted or unsubstituted picenyl, a substituted or unsubstituted furyl, a substituted or unsubstituted benzofuryl, a substituted or unsubstituted dibenzofuryl, a substituted or unsubstituted thienyl, a substituted or unsubstituted benzothienyl, a substituted or unsubstituted dibenzothienyl, a substituted or unsubstituted phenoxazinyl, a substituted or unsubstituted phenazinyl, a substituted or unsubstituted phenothiazinyl, a substituted or unsubstituted thioxazinyl, a substituted or unsubstituted thianthrenyl, a carbazole-derived group, an acridine-derived group, triarylamino and a triarylamine-derived group.

* * * * *